United States Patent
Shabat et al.

(10) Patent No.: US 11,241,507 B2
(45) Date of Patent: Feb. 8, 2022

(54) NEAR-INFRARED CHEMILUMINESCENT PROBES FOR IN-VIVO IMAGING

(71) Applicant: RAMOT AT TEL-AVIV UNIVERSITY LTD., Tel-Aviv (IL)

(72) Inventors: Doron Shabat, Tel-Aviv (IL); Ori Green, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 128 days.

(21) Appl. No.: 16/616,336

(22) PCT Filed: May 23, 2018

(86) PCT No.: PCT/IL2018/050558
§ 371 (c)(1),
(2) Date: Nov. 22, 2019

(87) PCT Pub. No.: WO2018/216013
PCT Pub. Date: Nov. 29, 2018

(65) Prior Publication Data
US 2020/0093942 A1    Mar. 26, 2020

Related U.S. Application Data

(60) Provisional application No. 62/510,385, filed on May 24, 2017.

(51) Int. Cl.
*A61B 5/00* (2006.01)
*A61B 8/00* (2006.01)
*A61B 10/00* (2006.01)
*A61K 49/00* (2006.01)
*C07D 407/10* (2006.01)

(52) U.S. Cl.
CPC ...... *A61K 49/0021* (2013.01); *A61K 49/0056* (2013.01); *C07D 407/10* (2013.01)

(58) Field of Classification Search
None
See application file for complete search history.

(56) References Cited

FOREIGN PATENT DOCUMENTS

| WO | 2006073424 A1 | 7/2006 |
| WO | 2017130191 A1 | 8/2017 |

OTHER PUBLICATIONS

Green et al.; "Opening a Gateway for Chemiluminescence Cell Imaging: Distinctive Methodology for Design of Bright Chemiluminescent Dioxetane Probes" Journal of the American Chemical Society 3, pp. 349-358. (2017).
Gu et al.; "Real-Time Tracking and In Vivo Visualization of β-Galactosidase Activity in Colorectal Tumor with a Ratiometric NIR Fluorescent Probe" Journal of the American Chemical Society, vol. 138, No. 16, pp. 5334-5340. (2016).
Hananya et al.; "Remarkable Enhancement of Chemiluminescent Signal by Dioxetane-Fluorophore Conjugates: Turn-ON Chemiluminescence Probes with Color Modulation for Sensing and Imaging" Journal of the American Chemical Society 138, Issue 40, pp. 13438-13446. (2016).
Zhang et al.; A near-infrared fluorescent probe for rapid detection of hydrogen peroxide in living cells, Tetrahedron vol. 71, Issue 29, pp. 4842-4845. (2015).
Green et al.; "Near-Infrared Dioxetane Luminophores with Direct Chemiluminescence Emission Mode" Journal of the American Chemical Society, vol. 139, Issue 37, pp. 13243-13248. (2017). Abstract only.
International Search Report dated Aug. 30, 2018. 4 pages.
Written Opinion dated Aug. 30, 2018. 6 pages.
Notification Concerning Transmittal of International Preliminary Report on Patentability and IPRP received in PCT/IL2018/050558 filed May 23, 2018, dated Dec. 5, 2019.

*Primary Examiner* — Michael G. Hartley
*Assistant Examiner* — Melissa J Perreira
(74) *Attorney, Agent, or Firm* — Knobbe, Martens, Olson & Bear, LLP

(57) ABSTRACT

The present invention provides turn-ON dioxetane-based chemiluminescence probes based on the Schapp's adamantylidene-dioxetane probe, which emit light in the near-infrared (NIR) region and are therefore useful for in vivo imaging, as well as compositions and uses thereof.

25 Claims, 4 Drawing Sheets

NEAR-INFRARED CHEMILUMINESCENT PROBES FOR IN-VIVO IMAGING

CROSS REFERENCE TO RELATED APPLICATIONS

This application is the U.S. National Phase under 35 U.S.C. § 371 of International Application No. PCT/IL2018/050558 filed May 23, 2018, designating the U.S. and published as WO 2018/216013 on Nov. 29, 2018, which claims the benefit of U.S. Provisional Application No. 62/510,385 filed May 24, 2017. Any and all applications for which a foreign or domestic priority claim is identified above and/or in the Application Data Sheet as filed with the present application are hereby incorporated by reference under 37 C.F.R. 1.57.

TECHNICAL FIELD

The present invention provides dioxetane-based chemiluminescence probes which emit light in the near-infrared (NIR) region and are therefore useful for in vivo imaging, and compositions thereof.

Abbreviations: ACN, acetonitrile; DCM, dichloromethane; DCMC, dicyano methylchromone; DMAP, 4-dimethylaminopyridine; DMF, N,N'-dimethylformamide; EtOAc, ethylacetate; Hex, hexane; HPLC, high pressure liquid chromatography; LDA, lithium diisopropylamide; MeOH, methanol; PBS, phosphate-buffered saline; PEG, polyethylene glycol; RLU, relative light units; RP-HPLC, reverse-phase high pressure liquid chromatography; TCF, tricyanofuran; THF, tetrahydrofuran; TLC, thin layer chromatography.

BACKGROUND ART

Optical imaging modalities have become powerful tools for noninvasive visualization of biomolecular systems and small animals in real-time with high spatial resolution. Moreover, imaging systems are relatively inexpensive, easy to use, portable, and adaptable to acquire physiological and functional information from microscopic to macroscopic levels.

There are several approaches in optical imaging, among them fluorescence is probably the most familiar. This technique is wildly used for imaging and monitoring various biological processes in-vivo. However, in fluorescence techniques complications arises from auto-fluorescence and light interferences, which typically increases the background noise. One way to overcome this obstacle is by using bioluminescence techniques, which minimize light interference since light is produced from within the animal. However, bioluminescence techniques rely heavily on transgenic cells that express the enzyme luciferase, which limits the development of luciferase-based bioluminescence methods.

Chemiluminescence, a relatively new imaging technique, offers significant advantages over fluorescence and bioluminescence techniques since light is generated by a specific chemical reaction that initiates light emission without further enzymatic dependency. So far, there have been several reports regarding chemiluminescent systems that have been used for in-vivo imaging. However, such systems usually depend on an energy transfer process from the chemiluminescent precursor to an emissive NIR dye. Furthermore, most chemiluminescent probes cannot be used as a general method for detection since their activation mechanism depends on an oxidation step that generates an unstable cyclic peroxide ring.

Schaap's adamatylidene 1,2-dioxetane probes (Scheme 1, structure I) are the only known compounds that do not require an oxidation step, since the energetic peroxide ring is thermally stable. This grants them a modular activating mechanism. As depicted in Scheme 1, Schaap's adamantylidene-dioxetane based chemiluminescence probe (structure I) is equipped with an analyte-responsive protecting group used to mask the phenol moiety of the probe. Removal of the protecting group by the analyte of interest generates an unstable phenolate-dioxetane species II, which decomposes through a chemiexcitation process to produce the excited intermediate benzoate ester III and adamantanone. The excited intermediate decays to its ground-state (benzoate ester IV) through emission of a blue light photon. Unfortunately, the chemiluminescent signal generated by Schaap's systems is not efficient under physiological conditions, and the blue photons released by these systems tend to be absorbed by organic tissues. In order to make Schaaps' dioxetane relevant to full body imaging, an increase of the light wavelength toward the NIR region is needed. This region is highly recommended for full body imaging, since NIR wavelengths can easily penetrate and are less scattered by living tissues. Up until recently, in-vitro and in-vivo imaging assays could not be applied without the use of a surfactant or complex supramolecular systems.

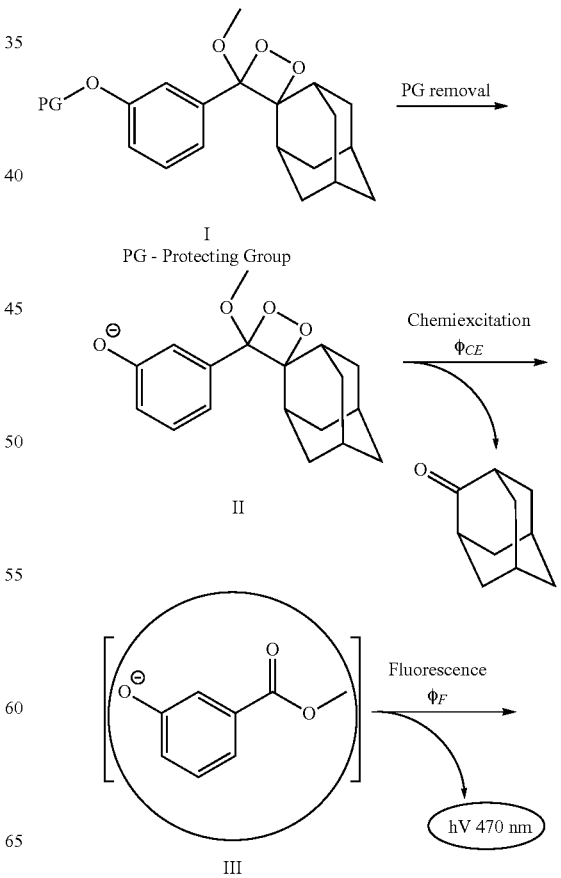

Scheme 1: Chemiluminescent activation pathway of Schaap's adamantylidene-dioxetane -continued

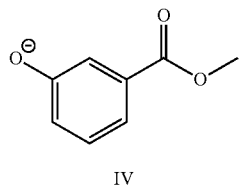

IV

International Publication No. WO 2017/130191 discloses chemiluminescence probes based on the Schapp's adamantylidene-dioxetane probe, wherein chemiluminescence emission is amplified through a direct mode of action, more particularly wherein the Schapp's adamantylidene-dioxetane probe is substituted at the ortho position of the phenolic ring with a π* acceptor group such as an acrylate and acrylonitrile electron-withdrawing group so as to increase the emissive nature of the benzoate species (Scheme 2). As shown in this publication, luminophores as disclosed allow for the enzymatic hydrolysis and the chemiexcitation process to occur concurrently under physiological conditions, with remarkable chemiluminescence intensities. Those luminophores are extremely bright in queues solutions; however, the light that is emitted by them is green (~530 nm) which is absorbed by tissue and thus, might cause difficulties when engaging whole animal imaging.

Scheme 2: Direct chemiluminescence mode obtained by substituting the Schapp's adamantylidene-dioxetane probe at the ortho position of the phenolic ring with a π* acceptor group

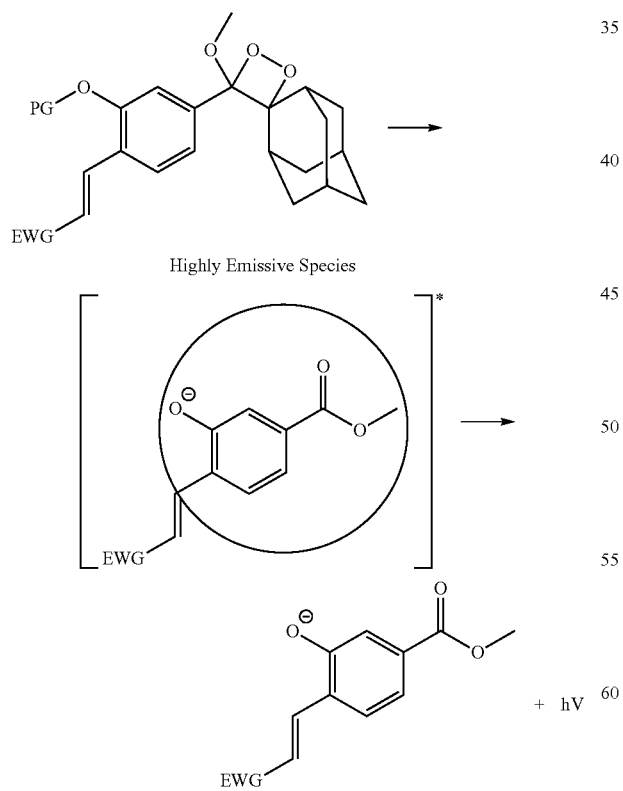

PG - Protecting Group
EWG - Electron Withdrawing Group

SUMMARY OF INVENTION

The present application discloses luminophores and chemiluminescence turn-ON probes based on those disclosed in International Publication No. WO 2017/130191, that efficiently emit NIR light under physiological conditions. The NIR region is highly recommended for full body imaging, because light at these wavelengths can penetrate trough tissue more easily and is less scattered by tissue. As shown herein, the luminophores and chemiluminescence turn-ON probes disclosed are able to monitor and image a specific analyte and enzyme activity both in-vitro and in-vivo using chemiluminescence techniques.

More particularly, in one aspect, the present invention provides a compound of the formula Ia or Ib:

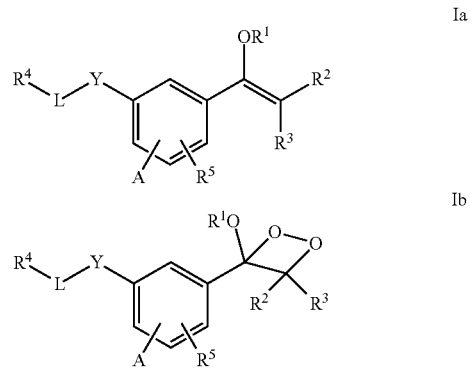

wherein
$R^1$ is selected from a linear or branched $(C_1-C_{18})$alkyl, or $(C_3-C_7)$cycloalkyl;
$R^2$ and $R^3$ each independently is selected from a branched $(C_3-C_{18})$alkyl or $(C_3-C_7)$cycloalkyl, or $R^2$ and $R^3$ together with the carbon atom to which they are attached form a fused, spiro or bridged cyclic or polycyclic ring,
$R^4$ is H, or a caging group such as:

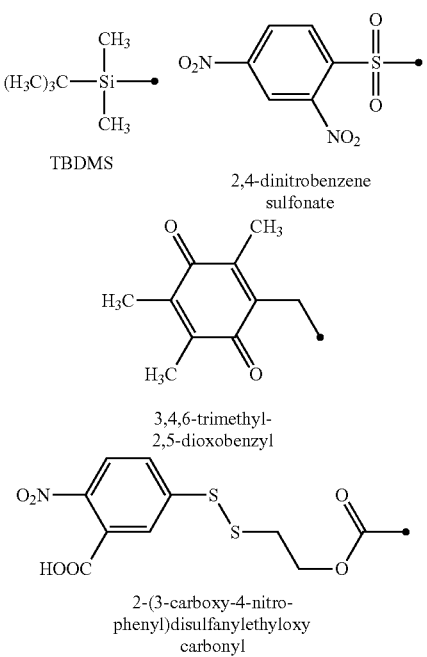

TBDMS 2,4-dinitrobenzene
sulfonate 3,4,6-trimethyl-
2,5-dioxobenzyl 2-(3-carboxy-4-nitro-
phenyl)disulfanylethyloxy
carbonyl

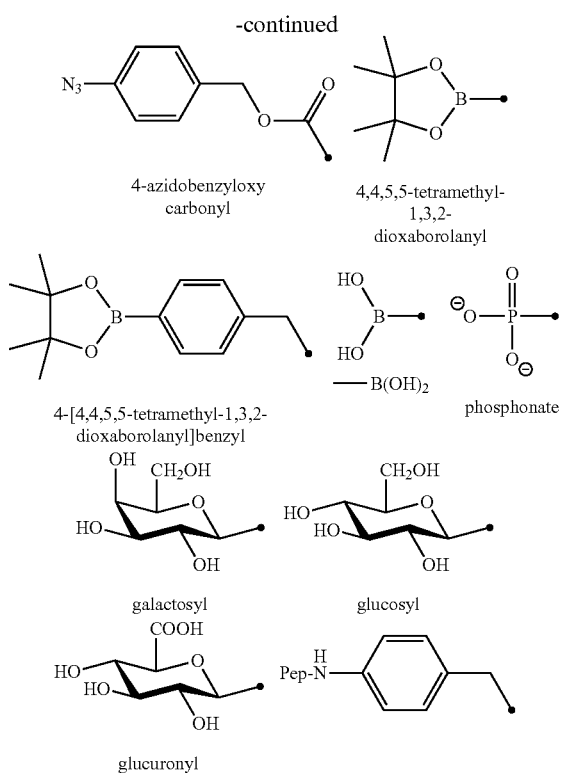

4-azidobenzyloxycarbonyl 4,4,5,5-tetramethyl-1,3,2-dioxaborolanyl

4-[4,4,5,5-tetramethyl-1,3,2-dioxaborolanyl]benzyl

B(OH)₂ phosphonate galactosyl glucosyl glucuronyl

Pep is a group comprising a peptide moiety consisting of at least two amino acid residues and linked to the aniline group via a carboxylic group of said peptide moiety;

L is absent or is a linker of the formula L1, L2 or L3, optionally substituted at the aromatic ring with one or more substituents each independently selected from $(C_1-C_{18})$alkyl or $(C_3-C_7)$cycloalkyl, wherein M is absent or is —O— or —NH—, and the asterisk represents the point of attachment to the group Y, provided that M is —O— or —NH— unless $R^4$ is 4,4,5,5-tetramethyl-1,3,2-dioxaborolanyl or —B(OH)₂, and when $R^4$ is H, L is absent;

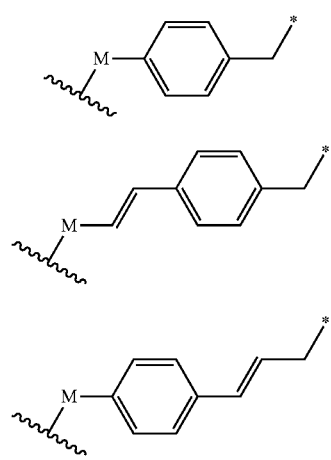

Y is absent or is —O—, provided that Y is —O— unless $R^4$ is 4,4,5,5-tetramethyl-1,3,2-dioxaborolanyl or —B(OH)₂, and L is absent;

$R^5$ is H, or represents at least one electron acceptor group such as halogen, —NO₂, —CN, —COOR⁶, —C(=O)R⁶ and —SO₂R⁶, each independently attached either ortho or para to the —Y-L-R⁴ group;

$R^6$ each independently is H or —$(C_1-C_{18})$alkyl; and

A represents one or two π* acceptor groups, each independently attached either ortho or para to the —Y-L-R⁴ group and selected from —CN or —CH=CH-E, wherein E is (a) —CN, —COOH, or —COO$(C_1-C_{18})$alkyl optionally interrupted in the alkylene chain with one or more —O— groups; (b) 4-pyridinyl, methylpyridinium-4-yl, 3,3-dimethyl-3H-indolyl, or 1,3,3-trimethyl-3H-indol-1-ium-2-yl, optionally substituted at one or more of the carbon atoms of the aromatic or heteroaromatic ring with a substituent each independently selected from halogen, —CN, —COOH, —COOR, or —C(O)R, wherein R is —$(C_1-C_{18})$alkyl; (c) 4-(dicyanomethylene)-4H-chromen-2-yl, 4H-chromen-2-yl-4-one, 9-(dicyanomethylene)-9H-xanthen-3-yl, 9H-xanthen-3-yl-9-one, 2-dicyanomethylenemethyl-thieno[3,2-b]thiophene-5-yl, 3-methylbenzo[d]thiazol-2-yl-3-ium, tetrathiafulvalenyl, 1,2,3,5,6,7-hexahydropyrido[3,2,1-ij]quinolin-9-yl, benzo[d]oxazol-2-yl, benzo[d]thiazol-2-yl, 1H-benzo[d]imidazol-2-yl, 2,6-di-tert-butylpyrylium-4-yl, 1-methylquinolin-1-ium-4-yl, or 4-dicyanomethylene-2-methyl-4H-pyran-6-yl, optionally substituted at one or more of the carbon atoms of the aromatic or heteroaromatic ring with a substituent each independently selected from halogen, —CN, —COOH, —COOR, or —C(O)R, wherein R is —$(C_1-C_{18})$alkyl; or (d) 5,5-dimethyl-3-cyano-2-dicyanomethylene-2,5-dihydrofuran-4-yl, or 5,5-dimethyl-3-cyano-2-oxo-2,5-dihydrofuran-4-yl, provided that at least one of said π* acceptor groups is —CH=CH-E, wherein E is selected from groups (c) or (d).

In another aspect, the present invention provides a composition, e.g., a pharmaceutical composition, comprising a dioxetane-based chemiluminescence probe as disclosed herein, i.e., a compound of the formula Ia/Ib as defined above, and a carrier, e.g., a pharmaceutically acceptable carrier. The compounds and compositions of the invention may be used for diagnostics or imaging of reporter genes, enzymes, and chemical analytes both in vitro and in vivo.

In a further aspect, the present invention thus relates to a dioxetane-based chemiluminescence probe as disclosed herein, i.e., a compound of the formula Ia/Ib as defined above, or a pharmaceutical composition comprising said compound, for use in vivo in diagnostics or imaging, more specifically, for determining the presence, or measuring the level, of a reporter gene, an enzyme, or a chemical analyte in vivo.

In yet another aspect, the present invention relates to a method for determining the presence, or measuring the level, of an analyte in a sample, e.g., a biological sample such as a bodily fluid, a bodily fluid-based solution or a tissue biopsy sample, said method comprising (i) contacting said sample with a compound of the formula Ia/Ib as defined above wherein $R^4$ is a group cleavable by said analyte, or a composition comprising said compound, to thereby hydrolyze said compound to an emissive species by said analyte, when present in said sample; and (ii) detecting the chemiluminescence emission of said emissive species.

chemiluminescence imaging of Probe 1a [5 μM] in HEK293 cells (1B); and quantification of signal intensities evolving from HEK293 cells (1C).

Figure 2:
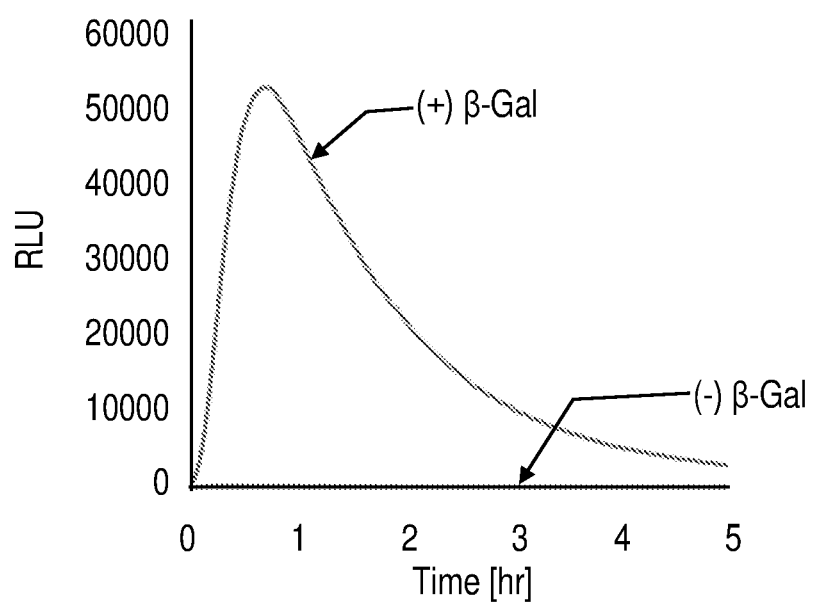

FIG. 2 shows the chemiluminescent kinetic profile of Probe 3a [1 μM] in PBS (100 mM) 7.4, with 10% serum in the presence and absence of β-galactosidase 1.5 EU/mL at 37° C. (right).

Figure 3:
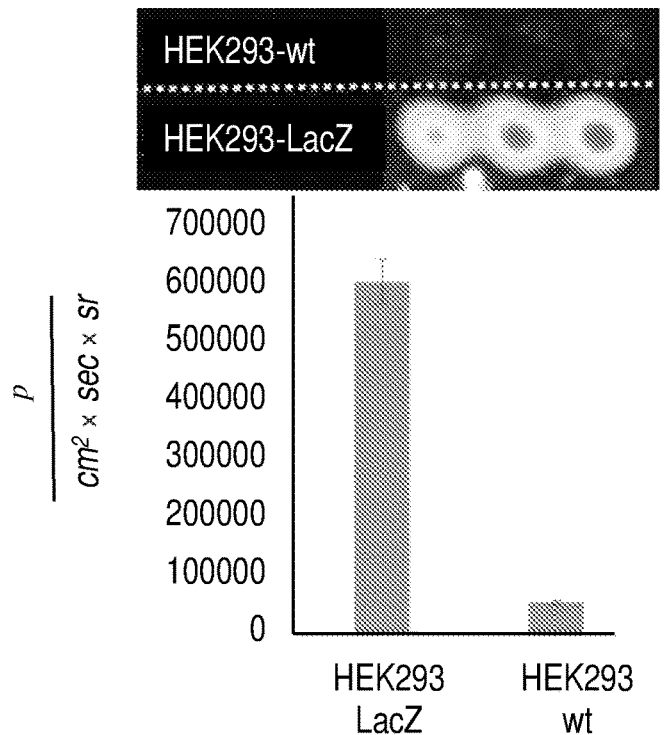

FIG. 3 shows chemiluminescence imaging of Probe 3a in HEK293-wt cells and HEK293-LacZ cells (top); and quantification of signal intensities evolving from Heck293 cells (bottom). Images were obtained following 20 minutes incubation with cell culture medium containing Probe 3a (5 μM), and were recorded on BioSpace Lab PhotonIMAGER™.

Figure 4A:
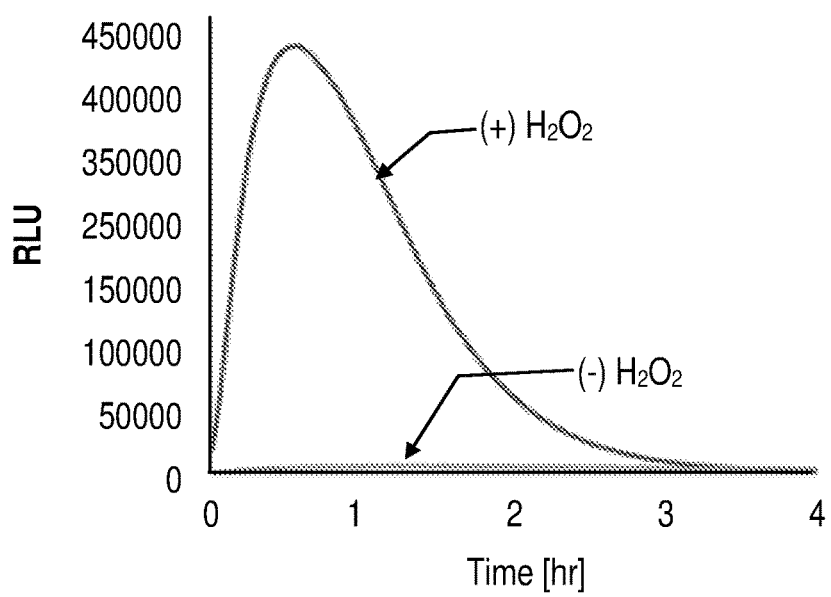
Figure 4B:
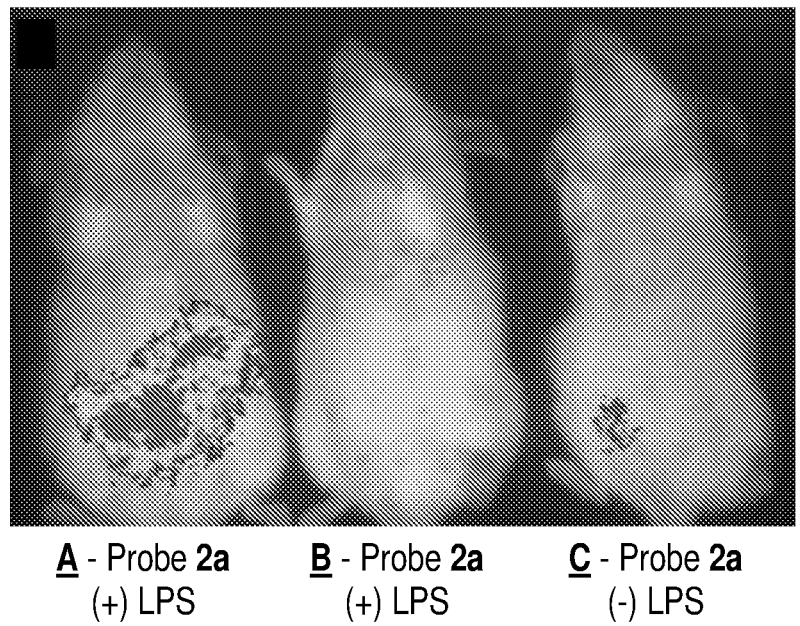
Figure 4C:
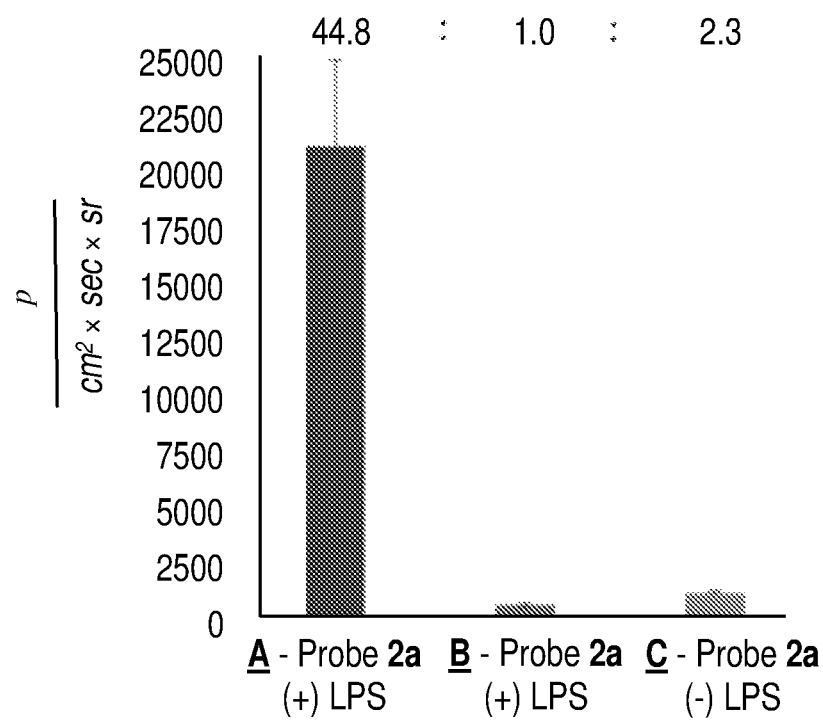

FIGS. 4A-4C show the chemiluminescent kinetic profile of Probe 2a [10 μM] in serum, in the presence and absence of $H_2O_2$ [50 μM] (4A); in-vivo imaging of endogenous $H_2O_2$ in the peritoneal cavity of mice during an LPS-induced inflammatory response, using probes 2a and 2b. Images of mice were recorded on BioSpace Lab PhotonIMAGER™. Group A: 1 mL of 0.1 mg/mL LPS was injected into the peritoneal cavity of mice, followed 4 h later by an IP injection of Probe 2a [100 μM, 100 μL in PBS]. Group B: 1 mL of 0.1 mg/mL LPS was injected into the peritoneal cavity of mice, followed 4 h later by an IP injection of Probe 2b [100 μM, 100 μL in PBS]. Group C: 1 mL PBS 7.4 was injected into the peritoneal cavity of mice, followed 4 h later by an IP injection of Probe 2a [100 μM, 100 μL in PBS 7.4] (4B); and quantification of signal intensities evolved from each group of mice (4C).

DETAILED DESCRIPTION

In one aspect, the present invention provides a turn-ON dioxetane-based chemiluminescence probe, more specifically a compound of the formula Ia or Ib as defined above.

The term "alkyl" typically means a linear or branched hydrocarbon radical having, e.g., 1-18 carbon atoms and includes methyl, ethyl, n-propyl, isopropyl, n-butyl, sec-butyl, isobutyl, tert-butyl, n-pentyl, 2,2-dimethylpropyl, n-hexyl, n-heptyl, n-octyl, and the like.

The term "alkylene" refers to a linear or branched divalent hydrocarbon radical derived after removal of hydrogen atom from an alkyl. The term "alkylene chain" refers to a group of the formula —$(CH_2)_n$— derived after removal of two hydrogen atoms from a linear hydrocarbon of the formula $C_nH_{2n+2}$.

The term "cycloalkyl" means a mono- or bicyclic saturated hydrocarbyl group having, e.g., 3-7 carbon atoms such as cyclopropyl, cyclobutyl, cyclopentyl, cyclohexyl, cycloheptyl, and the like, that may be substituted, e.g., by one or more alkyl groups.

The term "aryl" denotes an aromatic carbocyclic group having, e.g., 6-14, carbon atoms consisting of a single ring or condensed multiple rings such as, but not limited to, phenyl, naphthyl, phenanthryl, and biphenyl. The aryl may optionally be substituted by one or more groups each independently selected from halogen, ($C_1$-$C_8$)alkyl, —O—($C_1$-$C_8$)alkyl, —COO($C_1$-$C_8$)alkyl, —CN, and —$NO_2$.

The term "electron acceptor group" as used herein refers to a group of atoms with a high electron affinity. Non-limiting examples of such groups include halogen, —$NO_2$, —$SO_2$R, —CN, —C(=O)R, —C(=O)OR, and C(=O)$NR_2$, wherein R each independently may be, e.g., hydrogen, linear or branched ($C_1$-$C_{10}$)alkyl, or ($C_4$-$C_{10}$)aryl. Particular such electron acceptor groups include halogen, —$NO_2$, —$SO_2$R, —CN, —C(=O)R, and —C(=O)OR, wherein R each independently is H or —($C_1$-$C_{18}$)alkyl.

The term "halogen" as used herein refers to a halogen and includes fluoro, chloro, bromo, and iodo, but it is preferably fluoro or chloro.

The term "caging group" as used herein refers to an alcohol protecting group as well as to certain cleavable groups including enzyme cleavable groups such as monosaccharide moieties linked through a carbon atom thereof. Particular protecting/caging groups are those listed above (see Table 1).

The term "amino acid" as used herein refers to an organic compound comprising both amine and carboxylic acid functional groups, which may be either a natural or non-natural amino acid. The twenty-two amino acids naturally occurring in proteins are aspartic acid (Asp), tyrosine (Tyr), leucine (Leu), tryptophan (Trp), arginine (Arg), valine (Val), glutamic acid (Glu), methionine (Met), phenylalanine (Phe), serine (Ser), alanine (Ala), glutamine (Gln), glycine (Gly), proline (Pro), threonine (Thr), asparagine (Asn), lysine (Lys), histidine (His), isoleucine (Ile), cysteine (Cys), selenocysteine (Sec), and pyrrolysine (Pyl). Non-limiting examples of other amino acids include citrulline (Cit), diaminopropionic acid (Dap), diaminobutyric acid (Dab), ornithine (Orn), aminoadipic acid, β-alanine, 1-naphthylalanine, 3-(1-naphthyl)alanine, 3-(2-naphthyl)alanine, γ-aminobutiric acid (GABA), 3-(aminomethyl) benzoic acid, p-ethynyl-phenylalanine, p-propargly-oxy-phenylalanine, m-ethynyl-phenylalanine, p-bromophenylalanine, p-iodophenylalanine, p-azidophenylalanine, p-acetylphenylalanine, norleucine (Nle), azidonorleucine, 6-ethynyl-tryptophan, 5-ethynyl-tryptophan, 3-(6-chloroindolyl)alanine, 3-(6-bromoindolyl)alanine, 3-(5-bromoindolyl)alanine, azidohomoalanine, p-chlorophenylalanine, α-aminocaprylic acid, O-methyl-L-tyrosine, N-acetylgalactosamine-α-threonine, and N-acetylgalactosamine-α-serine.

The term "amino acid residue" as used herein refers to a residue of an amino acid after removal of hydrogen atom from an amino group thereof, e.g., its α-amino group or side chain amino group if present, and —OH group from a carboxyl group thereof, e.g., its α-carboxyl group or side chain carboxyl group if present.

The term "peptide" refers to a short chain of amino acid monomers (residues), e.g., a chain consisting of 2, 3, 4, 5, 6, 7, 8, 9, 10, 11, 12 or more amino acid residues, linked by peptide bonds, i.e., the covalent bond formed when a carboxyl group of one amino acid reacts with an amino group of another. The term "peptide moiety" as used herein denotes a moiety of a peptide as defined herein after removal of the hydrogen atom from either the terminal or a side chain carboxylic group thereof, and/or a hydrogen atom from either the terminal or a side chain amino group thereof.

The term "peptide bond" or "amide bond" as used herein refers to the covalent bond —C(O)NH— formed between two molecules, e.g., two amino acids, when a carboxyl group of one of the molecules reacts with an amino group of the other molecule, causing the release of a molecule of water.

TABLE 1

Certain caging groups with respect to compounds of the formula Ia/Ib

TBDMS

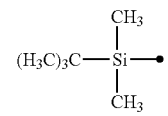

TABLE 1-continued

Certain caging groups with respect to compounds of the formula Ia/Ib 2,4-dinitrobenzenesulfonate

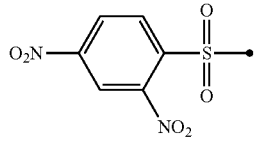

3,4,6-trimethyl-2,5-dioxobenzyl

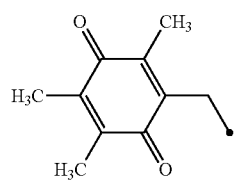

2-(3-carboxy-4-nitro-phenyl)disulfanylethyloxy carbonyl

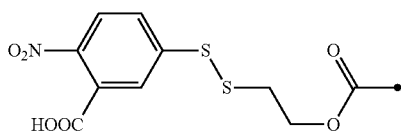

4-azidobenzyloxy carbonyl

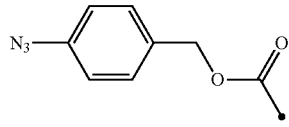

4,4,5,5-tetramethyl-1,3,2-dioxaborolanyl

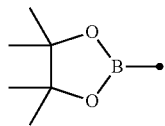

4-[4,4,5,5-tetramethyl-1,3,2-dioxaborolanyl]benzyl

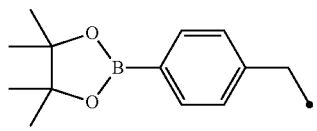

—B(OH)$_2$

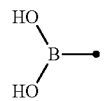

phosphonate

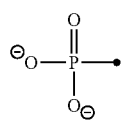

TABLE 1-continued

Certain caging groups with respect to compounds of the formula Ia/Ib galactosyl

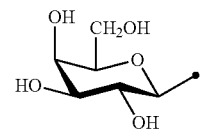

glucosyl

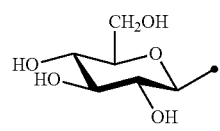

glucuronyl

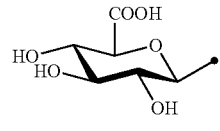

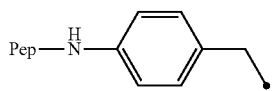

The term "amino protecting group" as used herein refers to any amino protecting group known in the art. An artisan skilled in the art can readily determine which protecting group(s) may be useful for the protection of the amino group(s), and standard methods are known in the art and are described in the literature. For example, suitable protecting groups are described in Green and Wuts, "*Protective Groups in Organic Synthesis*", John Wiley and Sons, Chapter 7, 1991. Preferred protecting groups include carbobenzyloxy (carboxybenzyl, Cbz), N-morpholinecarbonyl, p-methoxybenzyl carbonyl, tert-butyloxycarbonyl (BOC), 9-fluorenylmethyloxycarbonyl (FMOC), acetyl, benzyl, a carbamate group, p-methoxybenzyl (PMB), 3,4-dimethoxybenzyl (DMPM), p-methoxyphenyl (PMP), and a tosyl group.

The term "π* acceptor group" as used herein refers to any group containing a π* acceptor system capable of accepting electrons, e.g., those specifically listed above and shown in Table 2.

TABLE 2

Certain π* acceptor groups A of the formula —CH═CH—E (names refer to group E)

4-pyridinyl

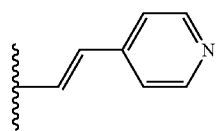 [SMILES: */C=C/c1ccncc1]

methylpyridinium-4-yl

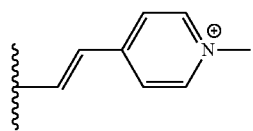 [SMILES: */C=C/c1cc[n+](C)cc1]

TABLE 2-continued

Certain π* acceptor groups A of the
formula —CH=CH—E (names refer to group E)

3,3-dimethyl-3H-indolyl 1,3,3-trimethyl-3H-indol-1-ium-2-yl 4-(dicyanomethylene)-4H-chromen-2-yl 4H-chromen-2-yl-4-one 9H-xanthen-3-yl-9-one 9-(dicyanomethylene)-9H-xanthen-3-yl 5,5-dimethyl-3-cyano-2-dicyanomethylene-
2,5-dihydrofuran-4-yl 5,5-dimethyl-3-cyano-
2-oxo-2,5-dihydrofuran-4-yl 2-dicyanomethylene methyl-
thieno[3,2-b]thiophene-5-yl tetrathiafulvalenyl 3-methylbenzo[d]thiazol-2-yl-3-ium 1,2,3,5,6,7-hexahydropyrido[3,2,1-
ij]quinolin-9-yl TABLE 2-continued Certain π* acceptor groups A of the
formula —CH=CH—E (names refer to group E)

O: benzo[d]oxazol-2-yl
S: benzo[d]thiazol-2-yl
NH: 1H-benzo[d]imidazol-2-yl

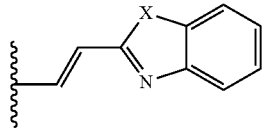

X = S, NH, O 2,6-di-tert-butylpyrylium-4-yl

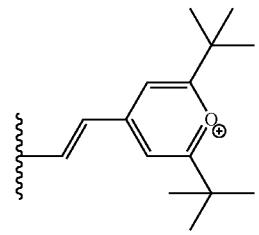 [SMILES: */C=C/c1cc(C(C)(C)C)[o+]c(C(C)(C)C)c1]

1-Methylquinolin-1-ium-4-yl

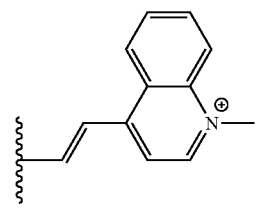 [SMILES: */C=C/c1cc[n+](C)c2ccccc12]

4-Dicyanomethylene-2-
methyl-4H-pyran-6-yl

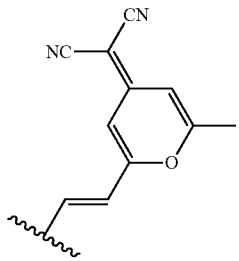 [SMILES: */C=C/C1=CC(=C(C#N)C#N)C=C(C)O1]

In certain embodiments, the invention provides a compound of the formula Ia or Ib, wherein $R^1$ is a linear or branched $(C_1-C_8)$alkyl, preferably $(C_1-C_4)$alkyl, more preferably methyl, ethyl, or isopropyl.

In certain embodiments, the invention provides a compound of the formula Ia or Ib, wherein $R^2$ and $R^3$ each independently is a branched $(C_3-C_{18})$alkyl or $(C_3-C_7)$cycloalkyl. In other embodiments, $R^2$ and $R^3$ together with the carbon atom to which they are attached form a fused, spiro or bridged polycyclic ring. In a particular such embodiment, $R^2$ and $R^3$ together with the carbon atom to which they are attached form adamantyl.

In certain embodiments, the invention provides a compound of the formula Ia or Ib, wherein $R^5$ is H, or an electron acceptor group selected from halogen or —CN attached either ortho or para to the —Y-L-$R^4$ group. In particular such embodiments, $R^5$ is halogen, e.g., Cl or F, or —CN, attached ortho to the —Y-L-$R^4$ group.

In certain embodiments, the invention provides a compound of the formula Ia or Ib, wherein A represents a π* acceptor group of the formula —CH=CH-E attached either ortho or para to the —Y-L-$R^4$ group, wherein E is (a) 4-(dicyanomethylene)-4H-chromen-2-yl, 4H-chromen-2-yl-4-one, 9-(dicyanomethylene)-9H-xanthen-3-yl, 9H-xanthen-3-yl-9-one, 2-dicyanomethylenemethyl-thieno[3,2-b]thiophene-5-yl, 3-methylbenzo[d]thiazol-2-yl-3-ium, tetrathiafulvalenyl, 1,2,3,5,6,7-hexahydropyrido[3,2,1-ij]quinolin-9-yl, benzo[d]oxazol-2-yl, benzo[d]thiazol-2-yl, 1H-benzo[d]imidazol-2-yl, 2,6-di-tert-butylpyrylium-4-yl, 1-methylquinolin-1-ium-4-yl, or 4-dicyanomethylene-2-methyl-4H-pyran-6-yl, optionally substituted at one or more of the carbon atoms of the aromatic or heteroaromatic ring; or (b) 5,5-dimethyl-3-cyano-2-dicyanomethylene-2,5-dihydrofuran-4-yl, or 5,5-dimethyl-3-cyano-2-oxo-2,5-dihydrofuran-4-yl. In particular such embodiments, E is 4-(dicyanomethylene)-4H-chromen-2-yl optionally substituted at one or more of the carbon atoms of the aromatic or heteroaromatic ring, or 5,5-dimethyl-3-cyano-2-dicyanomethylene-2,5-dihydrofuran-4-yl.

In certain embodiments, the invention provides a compound of the formula Ia or Ib, wherein A represents two π* acceptor groups, each independently attached either ortho or para to the —Y-L-$R^4$ group, wherein (i) one of said π* acceptor groups is of the formula —CH=CH-E, wherein E is (a) 4-(dicyanomethylene)-4H-chromen-2-yl, 4H-chromen-2-yl-4-one, 9-(dicyanomethylene)-9H-xanthen-3-yl, 9H-xanthen-3-yl-9-one, 2-dicyanomethylenemethyl-thieno[3,2-b]thiophene-5-yl, 3-methylbenzo[d]thiazol-2-yl-3-ium, tetrathiafulvalenyl, 1,2,3,5,6,7-hexahydropyrido[3,2,1-ij]quinolin-9-yl, benzo[d]oxazol-2-yl, benzo[d]thiazol-2-yl, 1H-benzo[d]imidazol-2-yl, 2,6-di-tert-butylpyrylium-4-yl, 1-methylquinolin-1-ium-4-yl, or 4-dicyanomethylene-2-methyl-4H-pyran-6-yl, optionally substituted at one or more of the carbon atoms of the aromatic or heteroaromatic ring; or (b) 5,5-dimethyl-3-cyano-2-dicyanomethylene-2,5-dihydrofuran-4-yl, or 5,5-dimethyl-3-cyano-2-oxo-2,5-dihydrofuran-4-yl; and (ii) the other one of said π* acceptor groups is of the formula —CH=CH-E, wherein E is —CN, —COOH, or —COO$(C_1-C_{18})$alkyl optionally interrupted in the alkylene chain with one or more —O— groups. In particular such embodiments, (i) one of said π* acceptor groups is of the formula —CH=CH-E, wherein E is 4-(dicyanomethylene)-4H-chromen-2-yl optionally substituted at one or more of the carbon atoms of the aromatic or heteroaromatic ring, or 5,5-dimethyl-3-cyano-2-dicyanomethylene-2,5-dihydrofuran-4-yl; and (ii) the other one of said π* acceptor groups is of the formula —CH=CH-E, wherein E is —CN, —COOH, or —COO$(C_1-C_{18})$alkyl optionally interrupted in the alkylene chain with one or more —O— groups.

In certain embodiments, the invention provides a compound of the formula Ia or Ib, wherein $R^1$ is a linear or branched $(C_1-C_8)$alkyl, preferably $(C_1-C_4)$alkyl, more preferably methyl, ethyl, or isopropyl; $R^2$ and $R^3$ together with the carbon atom to which they are attached form a fused, spiro or bridged polycyclic ring; $R^5$ is H, or an electron acceptor group selected from halogen or —CN, attached either ortho or para to the —Y-L-$R^4$ group; and A represents one or two π* acceptor groups each independently attached ortho or para to the —Y-L-$R^4$ group, wherein (i) one of said π* acceptor groups is of the formula —CH=CH-E, wherein E is (a) 4-(dicyanomethylene)-4H-chromen-2-yl, 4H-chromen-2-yl-4-one, 9-(dicyanomethylene)-9H-xanthen-3-yl, 9H-xanthen-3-yl-9-one, 2-dicyanomethylenemethyl-thieno[3,2-b]thiophene-5-yl, 3-methylbenzo[d]thiazol-2-yl-3-ium, tetrathiafulvalenyl, 1,2,3,5,6,7-hexahydropyrido[3,2,1-ij] quinolin-9-yl, benzo[d]oxazol-2-yl, benzo[d]thiazol-2-yl, 1H-benzo[d] imidazol-2-yl, 2,6-di-tert-butylpyrylium-4-yl, 1-methylquinolin-1-ium-4-yl, or 4-dicyanomethylene-2-methyl-4H-pyran-6-yl, optionally substituted at one or more of the carbon atoms of the aromatic or heteroaromatic ring; or (b) 5,5-dimethyl-3-cyano-2-dicyanomethylene-2,5-dihydrofuran-4-yl, or 5,5-dimethyl-3-cyano-2-oxo-2,5-dihydrofuran-4-yl; and (ii) the other one of said π* acceptor groups, when present, is of the formula —CH=CH-E, wherein E is —CN, —COOH, or —COO($C_1$-$C_{18}$)alkyl optionally interrupted in the alkylene chain with one or more —O— groups. In particular such embodiments, one of said π* acceptor groups is of the formula —CH=CH-E, wherein E is 4-(dicyanomethylene)-4H-chromen-2-yl optionally substituted at one or more of the carbon atoms of the aromatic or heteroaromatic ring, or 5,5-dimethyl-3-cyano-2-dicyanomethylene-2,5-dihydrofuran-4-yl; and the other one of said π* acceptor groups, when present, is of the formula —CH=CH-E, wherein E is —CN, —COOH, or —COO($C_1$-$C_{18}$)alkyl optionally interrupted in the alkylene chain with one or more —O— groups. More particular such embodiments are those wherein $R^1$ is methyl, ethyl, or isopropyl; $R^2$ and $R^3$ together with the carbon atom to which they are attached form adamantyl; $R^5$ is H, or is an electron acceptor group selected from halogen or —CN, attached ortho to the —Y-L-$R^4$ group; and A represents one or two π* acceptor groups, wherein one of said π* acceptor groups is of the formula —CH=CH-E, wherein E is 4-(dicyanomethylene)-4H-chromen-2-yl, or 5,5-dimethyl-3-cyano-2-dicyanomethylene-2,5-dihydrofuran-4-yl; and the other one of said π* acceptor groups, when present, is of the formula —CH=CH-E, wherein E is —CN, —COOH, —COOCH$_3$, —COOC(CH$_3$)$_3$, or —COO[(CH$_2$)$_2$—O]$_4$—CH$_3$.

In certain embodiments, the invention provides a compound of the formula Ia or Ib as defined in any one of the embodiments above, wherein Y is —O—; L is absent; and $R^4$ is H.

In certain embodiments, the invention provides a compound of the formula Ia or Ib as defined in any one of the embodiments above, wherein Y is —O—, L is absent, and $R^4$ is a caging group, i.e., an alcohol protecting group or a cleavable group, e.g., an enzyme cleavable group such as a monosaccharide moiety linked through a carbon atom thereof. In particular such embodiments, the caging group is one of those shown in Table 1 excluding 4,4,5,5-tetramethyl-1,3,2-dioxaborolanyl and —B(OH)$_2$, wherein each one of these caging groups represents a separate embodiment. More particular such embodiments are those wherein the caging group is, e.g., phosphonate or galactosyl.

In certain embodiments, the invention provides a compound of the formula Ia or Ib as defined in any one of the embodiments above, wherein Y is —O—, L is a linker of the formula L1, L2 or L3, wherein M is —O— or —NH—, and $R^4$ is a caging group. In particular such embodiments, the caging group is one of those shown in Table 1 excluding 4,4,5,5-tetramethyl-1,3,2-dioxaborolanyl and —B(OH)$_2$, wherein each one of these caging groups represents a separate embodiment. More particular such embodiments are those wherein the caging group is, e.g., galactosyl.

In certain embodiments, the invention provides a compound of the formula Ia or Ib as defined in any one of the embodiments above, wherein Y is absent, L is absent, and $R^4$ is the caging group 4,4,5,5-tetramethyl-1,3,2-dioxaborolanyl or —B(OH)$_2$.

In certain embodiments, the invention provides a compound of the formula Ia or Ib as defined in any one of the embodiments above, wherein Y is —O—; L is absent; and $R^4$ is a caging group of the formula:

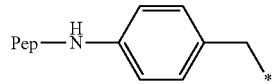

wherein Pep is a group comprising a peptide moiety consisting of at least two amino acid residues and linked to the aniline group via a carboxylic group of said peptide moiety. More particular such caging groups have the formula:

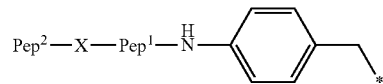

wherein $Pep^1$ is an enzyme cleavable peptide moiety, i.e., a moiety of an enzyme cleavable peptide, consisting of at least two amino acid residues and linked via a carboxylic group thereof to the aniline group, wherein said enzyme cleavable peptide moiety is optionally protected or linked, e.g., via an amide bond, through an amino group thereof to a PEG-containing group; X is absent, or is a linker linked to $Pep^1$ via an amide bond through either a carboxyl or amino group of $Pep^1$; and $Pep^2$ is absent, or a cell-penetrating peptide moiety linked to X either via an amide bond through an amino or carboxyl group thereof, or through a thiol group thereof, provided that X and $Pep^2$ are both either absent or present, and when $Pep^1$ is protected or linked to a PEG-containing group, X and $Pep^2$ are absent. In particular such embodiments, $Pep^1$ is a protease cleavable peptide moiety, i.e., a moiety of an amino acid sequence, optionally modified, that is cleavable by a protease, i.e., an enzyme capable of performing proteolysis (protein catabolism) by hydrolysis of peptide bonds, wherein removal of said cleavable group by the particular protease of interest generates an unstable phenolate-dioxetane species that decomposes through a chemiexcitation process to produce the excited intermediate, which then further decays to its ground-state through emission of NIR light. The protease referred to herein may be any protease such as a serine protease, a cysteine protease, a threonine protease, an aspartic protease, a glutamic protease, or a metalloprotease, i.e., a protease enzyme whose catalytic mechanism involves a metal (usually zinc). Examples of such proteases include, without limiting, cathepsins such as cathepsin A, B, C, D, E, F, G H, K, L1, L2, O, S, W and Z; legumain; prostate specific antigen (PSA); and matrix metalloproteases (MMP).

Particular such chemiluminescence probes may be used for detecting the presence or over expression of cathepsin B, a lysosomal cysteine protease involved in intracellular proteolysis, which is overexpressed in premalignant lesions and various pathological conditions, as well as in cancers, e.g., in tumor endothelial cells and many other tumor cells in the lysosome (Miller et al., 2009). Cathepsin B-cleavable peptides include, without limiting, peptides comprising, or consisting of, the amino acid sequence Val-Cit, Phe-Lys, or Gly-Phe-Leu-Gly (such peptides will be linked via the carboxylic group of the citrulline, lysine or glycine, respectively, to the aniline group of $R^4$).

Other particular such chemiluminescence probes may be used for detecting the presence or over expression of cathepsin K, a lysosomal cysteine protease involved in bone remodeling and resorption, which is expressed predominantly in osteoclasts and overexpressed extracellularly in bone neoplasms (Segal et al., 2009). Cathepsin K-cleavable peptides include, without limiting, peptides comprising, or consisting of, the amino acid sequence Gly-Gly-Pro-Nle (such peptides will be linked via the carboxylic group of the norleucine to the aniline group of $R^4$).

Yet other particular such chemiluminescence probes may be used for detecting the presence or over expression of legumain, a lysosomal enzyme that is overexpressed in tumor cells (Stern et al., 2009). Legumain-cleavable peptides include, without limiting, peptides comprising, or consisting of, the amino acid sequence Ala-Ala-Asn (such peptides will be linked via the carboxylic group of the asparagine to the aniline group of $R^4$).

Further particular such chemiluminescence probes may be used for detecting the presence or over expression of PSA, a member of the kallikrein-related protease family that is secreted by the epithelial cells of the prostate gland and used as a marker for prostate cancer or other prostate disorders. PSA-cleavable peptides include, without limiting, peptides comprising, or consisting of, the amino acid sequence His-Ser-Ser-Lys-Leu-Gln (such peptides will be linked via the carboxylic group of the glutamine to the aniline group of $R^4$).

Other particular such chemiluminescence probes may be used for detecting the presence or over expression of a MMP, i.e., a member of Zn-dependent endopeptidases that are collectively capable of hydrolyzing all proteins of the extracellular matrix, and thus play important roles in physiological processes such as tissue morphogenesis and repair; and contribute to cancer progression by promoting tumor cell invasion of the basement membrane and stroma, blood vessel penetration, and metastasis. Examples of MMPs include, without limiting, MMP9, that is critical for the formation of the pre-metastatic niche and has a distinct role in tumor angiogenesis by regulating the bioavailability of vascular endothelial growth factor, and MMP2.

In certain particular such embodiments, $Pep^1$ is a protease cleavable peptide moiety comprising, or consisting of, the amino acid sequence Val-Cit, Phe-Lys, Gly-Phe-Leu-Gly, Gly-Gly-Pro-Nle, Ala-Ala-Asn or His-Ser-Ser-Lys-Leu-Gln, wherein said amino acid sequence is linked via the carboxylic group of the citrulline, lysine, glycine, norleucine, asparagine or glutamine, respectively, to the aniline group; and optionally protected at an amino group thereof, or linked via an amide bond and through said amino group to a PEG-containing group, e.g., a PEG-containing group of the formula:

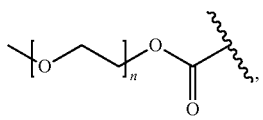

wherein n is an integer of 1 to 227.

In more particular such embodiments, $Pep^1$ is a peptide moiety of the sequence Val-Cit, Phe-Lys, Gly-Phe-Leu-Gly, Gly-Gly-Pro-Nle, Ala-Ala-Asn or His-Ser-Ser-Lys-Leu-Gln, linked via the carboxylic group of the citrulline, lysine, glycine, norleucine, asparagine or glutamine, respectively, to the aniline group, and either (i) protected at the α-amino group of the valine, phenylalanine, glycine, glycine, alanine or histidine, respectively, with an amino protecting group; or (ii) linked via the α-amino group of the valine, phenylalanine, glycine, glycine, alanine or histidine, respectively, to a PEG-containing group of the formula

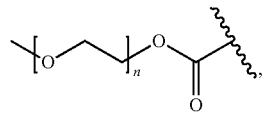

wherein n is an integer of 1 to 227.

In other particular such embodiments, $Pep^1$ is a protease cleavable peptide moiety comprising, or consisting of, the amino acid sequence Val-Cit, Phe-Lys, Gly-Phe-Leu-Gly, Gly-Gly-Pro-Nle, Ala-Ala-Asn or His-Ser-Ser-Lys-Leu-Gln, linked via the carboxylic group of the citrulline, lysine, glycine, norleucine, asparagine or glutamine, respectively, to the aniline group; X is a linker linked to $Pep^1$ via an amide bond through either a carboxyl or amino group of $Pep^1$; and $Pep^2$ is a cell-penetrating and solubilizing peptide moiety linked to X through a thiol group thereof. In more particular such embodiments, X is a linker of the formula:

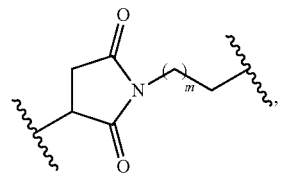

linked to $Pep^1$ via an amide bond through an amino group of $Pep^1$, wherein m is an integer of 1-20, and the alkylene chain of X is optionally interrupted with one or more —O— groups; and $Pep^2$ is a cell-penetrating and solubilizing peptide moiety of the sequence Cys-Gly-Lys-Arg-Lys, linked to X through the thiol group of the cysteine residue.

In certain specific embodiments, the chemiluminescence probe disclosed herein is a compound of the formula Ia or Ib, wherein $R^1$ is methyl; $R^2$ and $R^3$ together with the carbon atom to which they are attached form adamantyl; and (i) $R^5$ is H; A represents a 7π* acceptor group of the formula —CH=CH-E attached para to the —Y-L-$R^4$ group, wherein E is 4-(dicyanomethylene)-4H-chromen-2-yl; Y is —O—; L is absent; and $R^4$ is H (e.g., the compound identified herein as Luminophore 1]; (ii) $R^5$ is Cl attached ortho to the —Y-L-$R^4$ group; A represents a π* acceptor group of the formula —CH=CH-E attached ortho to the —Y-L-$R^4$ group, wherein E is 4-(dicyanomethylene)-4H-chromen-2-yl; Y is —O—; L is absent; and $R^4$ is H (e.g., the compound identified herein as Luminophore 4); (iii) $R^5$ is H; A represents two π* acceptor groups, wherein one of said π* acceptor groups is attached para to the —Y-L-$R^4$ group and is of the formula —CH=CH-E, wherein E is 4-(dicyanomethylene)-4H-chromen-2-yl, and the other one of said π* acceptor groups is attached ortho to the —Y-L-$R^4$ group and is of the formula —CH=CH-E, wherein E is —COOH; Y is —O—; L is absent; and $R^4$ is H (e.g., the compound identified herein as Luminophore 2); (iv) $R^5$ is H; A represents two π* acceptor groups, wherein one of said π* acceptor groups is attached para to the —Y-L-$R^4$ group and is of the formula —CH=CH-E, wherein E is 5,5-dimethyl-3-cyano-2-dicyanomethylene-2,5-dihydrofuran-4-yl, and the other one of said π* acceptor groups is attached ortho to the —Y-L-R⁴ group and is of the formula —CH=CH-E, wherein E is —COOH; Y is —O—; L is absent; and R⁴ is H (e.g., the compound identified herein as Luminophore 3); (v) R⁵ is H; A represents a π* acceptor group of the formula —CH=CH-E attached para to the —Y-L-R⁴ group, wherein E is 4-(dicyanomethylene)-4H-chromen-2-yl; Y is —O—; L is absent; and R⁴ is galactosyl (e.g., the compound identified herein as Probe 1a); (vi) R⁵ is H; A represents two π* acceptor groups, wherein one of said π* acceptor groups is attached para to the —Y-L-R⁴ group and is of the formula —CH=CH-E, wherein E is 4-(dicyanomethylene)-4H-chromen-2-yl, and the other one of said π* acceptor groups is attached ortho to the —Y-L-R⁴ group and is of the formula —CH=CH-E, wherein E is —COOH; Y is absent; L is absent; and R⁴ is 4,4,5,5-tetramethyl-1,3,2-dioxaborolanyl (e.g., the compound identified herein as Probe 2a); or (vii) R⁵ is H; A represents two π* acceptor groups, wherein one of said π* acceptor groups is attached para to the —Y-L-R⁴ group and is of the formula —CH=CH-E, wherein E is 5,5-dimethyl-3-cyano-2-dicyanomethylene-2,5-dihydro-furan-4-yl, and the other one of said π* acceptor groups is attached ortho to the —Y-L-R⁴ group and is of the formula —CH=CH-E, wherein E is —COO[(CH₂)₂—O]₄—CH₃; Y is —O—; L is L1 wherein M is —O—; and R⁴ is galactosyl (e.g., the compound identified herein as Probe 3a). The specific compounds disclosed herein are shown in Table 3.

In another aspect, the present invention provides a composition comprising a dioxetane-based chemiluminescence probe as disclosed herein, i.e., a compound of the formula Ia/Ib as defined in any one of the embodiments above, and a carrier. Particular such compositions are pharmaceutical compositions comprising said chemiluminescence probe and a pharmaceutically acceptable carrier.

In specific embodiments, the composition of the present invention comprises a chemiluminescence probe of the formula Ia/Ib selected from those listed in Table 3.

TABLE 3

Specific compounds of the formula Ia/Ib disclosed herein

Luminophore 1

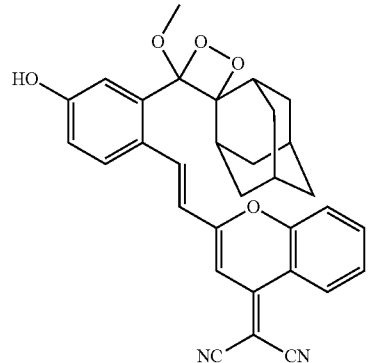 [SMILES: COC1(c2cc(O)ccc2/C=C/C2=CC(=C(C#N)C#N)c3ccccc3O2)OOC12C1CC3CC(C1)CC2C3]

Luminophore 2

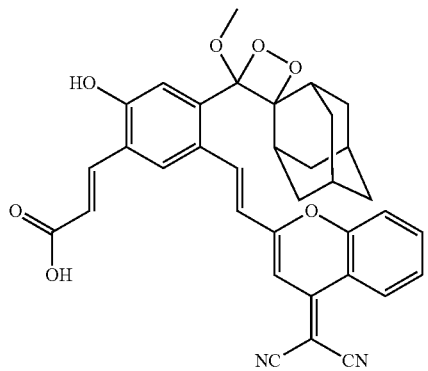 [SMILES: COC1(c2cc(O)c(/C=C/C(=O)O)cc2/C=C/C2=CC(=C(C#N)C#N)c3ccccc3O2)OOC12C1CC3CC(C1)CC2C3]

TABLE 3-continued
Specific compounds of the formula Ia/Ib disclosed herein
Luminophore 3
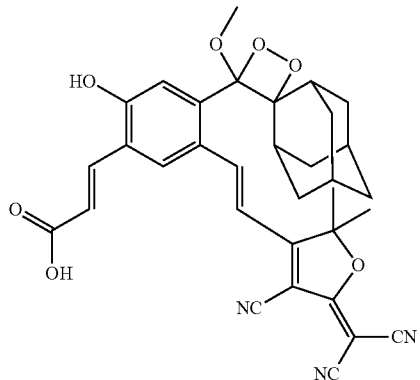 [SMILES: COC1(c2cc(O)c(/C=C/C(=O)O)cc2/C=C/C2=C(C#N)C(=C(C#N)C#N)OC2(C)C)OOC12C1CC3CC(C1)CC2C3]
Luminophore 4
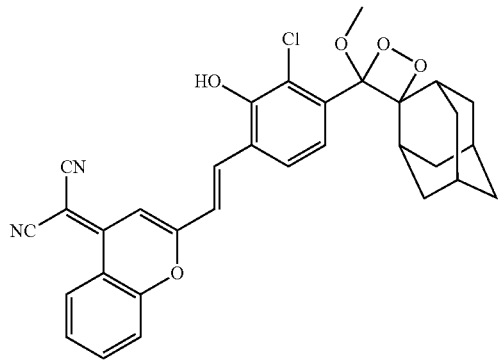 [SMILES: COC1(c2ccc(/C=C/C3=CC(=C(C#N)C#N)c4ccccc4O3)c(O)c2Cl)OOC12C1CC3CC(C1)CC2C3]
Probe 1a
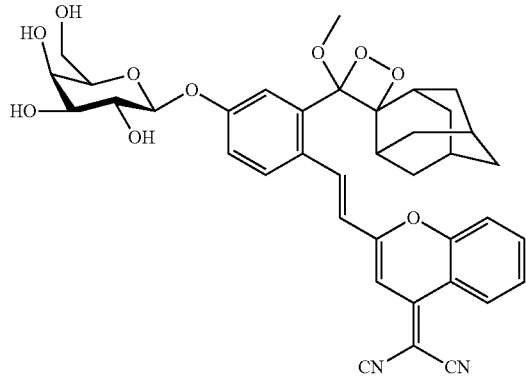
Probe 2a
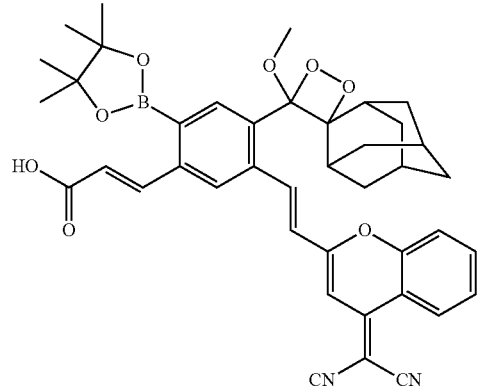

TABLE 3-continued

Specific compounds of the formula Ia/Ib disclosed herein

Probe 3a

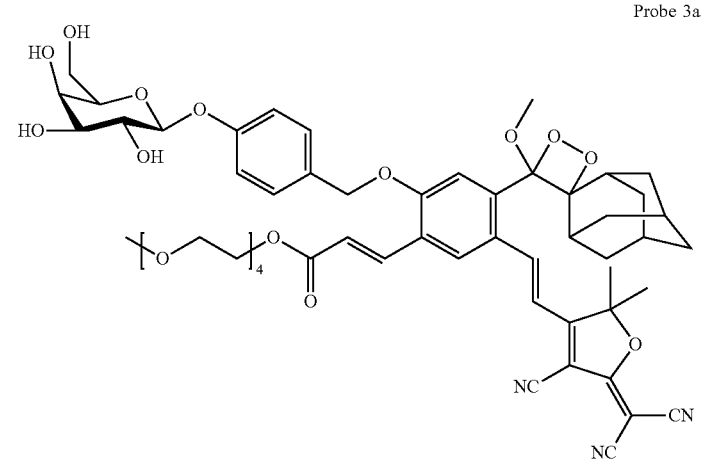

The chemiluminescence probes of the present invention emit NIR light under physiological conditions with high efficiency and may thus be used for diagnostics and/or imaging both in vitro and in vivo. Triggered chemiluminescence emission can provide a highly sensitive readout of biological analytes. Chemiluminescence does not require light excitation, thereby drastically reducing background from autofluorescence and photoactivation of functional groups. Whereas bioluminescence, i.e., chemiluminescence derived from living systems that express bioluminescent enzymes such as luciferase, has found wide application for preclinical analysis of biological parameters using genetically modified organisms, small molecule chemiluminescence can be used with wild-type animals and opens up exciting opportunities for clinical imaging.

In a further aspect, the present invention thus relates to (i) a dioxetane-based chemiluminescence probe of the formula Ia/Ib as defined in any one of the embodiments above; or (ii) a pharmaceutical composition comprising said chemiluminescence probe, for use in vivo in diagnostics or imaging.

In other words, the present invention relates to a method for determining the presence, or measuring the level, of an analyte in an individual in need, said method comprising (i) administering to said individual a compound of the formula Ia/Ib as defined in any one of the embodiments above wherein $R^4$ is a group cleavable by said analyte, or a composition comprising said compound, to thereby hydrolyze said compound to an emissive species by said analyte, when present in said individual; and (ii) detecting the chemiluminescence emission of said emissive species. According to the present invention, the chemiluminescence probe can be administered systemically or locally, e.g., to a particular organ of said individual, so as to determine the presence, or measure the level, of said analyte in general, or in particular said organ.

In yet another aspect, the present invention relates to a method for determining the presence, or measuring the level, of an analyte in a sample, i.e., in vitro, said method comprising (i) contacting said sample with a compound of the formula Ia/Ib as defined in any one of the embodiments above wherein $R^4$ is a group cleavable by said analyte, or a composition comprising said compound, to thereby hydrolyze said compound to an emissive species by said analyte, when present in said sample; and (ii) detecting the chemiluminescence emission of said emissive species.

The sample analyzed according to this method may be any sample, e.g., a biological sample. The term "biological sample" as used herein refers to a tissue biopsy sample; a bodily fluid such as an amniotic fluid, aqueous humour, vitreous humour, bile, blood serum, breast milk, cerebrospinal fluid, cerumen (earwax), endolymph, perilymph, female ejaculate, gastric juice, mucus, peritoneal fluid, saliva, sebum (skin oil), semen, sweat, tears, vaginal secretion, vomit and urine; or a bodily fluid-based solution, i.e., an aqueous solution in which a bodily fluid is dissolved.

Chemiluminescence probes as disclosed herein, wherein $R^4$ is a caging group cleavable by a particular enzyme may be used, either per se or when formulated as a composition, for determining the presence, or measuring the level, of said enzyme either in vivo or in a biological sample. Other probes, wherein $R^4$ is a caging group cleavable by a particular chemical compound may be used, either per se or when formulated as a composition, for determining the presence, or measuring the level, of said chemical compound either in vivo or in a biological sample.

Chemiluminescence probes as disclosed herein, wherein $R^4$ is a caging group of the formula:

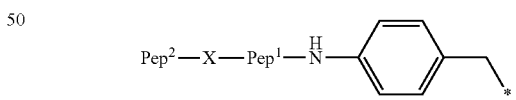

as defined above wherein $Pep^1$ is an enzyme cleavable peptide moiety, e.g., a protease cleavable peptide moiety, may be used, either per se or when formulated as a composition, for determining the presence, or measuring the level, of said enzyme either in vivo or in a biological sample, i.e., in vitro. For example, such probes wherein $Pep^1$ is a protease cleavable peptide moiety may be used for determining the presence, or measuring the level, of a protease such as a serine protease, a cysteine protease, a threonine protease, an aspartic protease, a glutamic protease, or a metalloprotease. Examples of such proteases include, without limiting, cathepsins such as cathepsin A, B, C, D, E, F, G, H, K, L1, L2, O, S, W and Z, legumain, PSA, and a MMP such as MMP9 and MMP2. Non-limiting examples of groups cleavable by cathepsin B or K, legumain, or PSA are described above.

Chemiluminescence probes as disclosed herein, wherein $R^4$ is a caging group cleavable by the enzyme β-galactosidase, e.g., galactosyl, may be used, either per se or when formulated as a composition, for determining the presence, or measuring the level, of said enzyme either in vivo or in a biological sample.

Chemiluminescence probes as disclosed herein, wherein $R^4$ is a caging group cleavable by the enzyme alkaline-phosphatase, e.g., phosphonate, may be used, either per se or when formulated as a composition, for determining the presence, or measuring the level, of said enzyme either in vivo or in a biological sample.

Chemiluminescence probes as disclosed herein, wherein $R^4$ is a caging group cleavable by the antioxidant glutathione, e.g., 2,4-dinitrobenzene sulfonate, may be used, either per se or when formulated as a composition, for determining the presence, or measuring the level, of said antioxidant either in vivo or in a biological sample.

Chemiluminescence probes as disclosed herein, wherein $R^4$ is a caging group cleavable by hydrogen peroxide ($H_2O_2$), e.g., 4,4,5,5-tetramethyl-1,3,2-dioxaborolanyl, or 4-[4,4,5,5-tetramethyl-1,3,2-dioxaborolanyl]benzyl, may be used, either per se or when formulated as a composition, for determining the presence, or measuring the level, of $H_2O_2$ either in vivo or in a biological sample.

Pharmaceutical compositions according to the present invention may be prepared by conventional techniques, e.g., as described in Remington: The Science and Practice of Pharmacy, 19$^{th}$ Ed., 1995. The compositions can be prepared, e.g., by uniformly and intimately bringing the active agent, i.e., the dioxetane-based chemiluminescence probe of the formula Ia or Ib, into association with a liquid carrier, a finely divided solid carrier, or both, and then, if necessary, shaping the product into the desired formulation. The compositions may be in liquid, solid or semisolid form and may further include pharmaceutically acceptable fillers, carriers, diluents or adjuvants, and other inert ingredients and excipients. In one embodiment, the pharmaceutical composition of the present invention is formulated as nanoparticles.

A pharmaceutical composition according to the present invention can be formulated for any suitable route of administration, e.g., for parenteral administration such as intravenous, intraarterial, intrathecal, intrapleural, intratracheal, intraperitoneal, intramuscular or subcutaneous administration, topical administration, oral or enteral administration, or for inhalation. In particular embodiments, such a composition is formulated for intravenous or intraperitoneal administration, or for subcutaneous administration, e.g., by an alzet pump implanted subcutaneous.

The pharmaceutical composition of the invention may be in the form of a sterile injectable aqueous or oleaginous suspension, which may be formulated according to the known art using suitable dispersing, wetting or suspending agents. The sterile injectable preparation may also be a sterile injectable solution or suspension in a non-toxic parenterally acceptable diluent or solvent. Acceptable vehicles and solvents that may be employed include, e.g., water, Ringer's solution and isotonic sodium chloride solution.

The chemiluminescence emission of the probes of the present invention can be detected utilizing any technique or procedure known in the art.

Optical molecular imaging is a promising technique that provides a high degree of sensitivity and specificity in tumor margin detection. Furthermore, existing clinical applications have proven that optical molecular imaging is a powerful intraoperative tool for guiding surgeons performing precision procedures, thus enabling radical resection and improved survival rates. An example of a clinically approved instrument for minimally invasive surgical procedures under fluorescence guidance is the da Vinci Surgical System (Haber et al., 2010). This instrument is featured with a 3D HD vision system for a clear and magnified view inside a patient's body and allows surgeons to perform complex and routine procedures through a few small openings, similar to traditional laparoscopy. In addition, the following systems have already been applied in surgeries for breast cancer, liver metastases and bypassing graft surgery: The Hamamatsu's Photodynamic Eye (PDE™), Artemis™ and Novadaq SPY™ (Novadaq Technologies Inc., Toronto, Canada) (Chi et al., 2014). Several existing intraoperative NIR fluorescence molecular imaging systems were evaluated in clinical trials; including, Fluobeam®, FLARE™ and GXMI Navigator. They have played an important role in operation convenience, improving image assessment and increasing detection depth (Chi et al., 2014).

In recent years, there has been a great progress in the development of cameras and lasers for optical fluorescence imaging in the IR range (Mieog et al., 2011; Troyan et al., 2009). In parallel, there is a vast clinical use of low MW organic dyes such as ICG and methylene blue for determining cardiac output, hepatic function and liver blood flow, and for ophthalmic angiography. In 2015, the fluorescence imaging system, Xiralite®, gained FDA approval for visualization of microcirculation in the hands (for inflammation and perfusion-related disorders).

The invention will now be illustrated by the following non-limiting Examples.

EXAMPLES

Study 1. Synthesis and Efficacy of Chemiluminescence Probes as Disclosed Herein
Synthesis of Luminophores 1-4 and Probes
General Methods All reactions requiring anhydrous conditions were performed under an argon atmosphere. All reactions were carried out at room temperature unless stated otherwise. Chemicals and solvents were either A.R. grade or purified by standard techniques. TLC: silica gel plates Merck 60 F254: compounds were visualized by irradiation with UV light. Column chromatography (FC): silica gel Merck 60 (particle size 0.040-0.063 mm), eluent given in parentheses. RP-HPLC: C18 5u, 250×4.6 mm, eluent given in parentheses. Preparative RP-HPLC: C18 5u, 250×21 mm, eluent given in parentheses. $^1$H-NMR spectra were recorded using Bruker Avance operated at 400 MHz. $^{13}$C-NMR spectra were recorded using Bruker Avance operated at 100 MHz. Chemical shifts were reported in ppm on the δ scale relative to a residual solvent (CDCl$_3$: δ=7.26 for $^1$H-NMR and 77.16 for $^{13}$C-NMR, DMSO-d$_6$: δ=2.50 for $^1$H-NMR and 39.52 for $^{13}$C-NMR). Mass spectra were measured on Waters Xevo TQD. Fluorescence and chemiluminescence were recorded on Molecular Devices Spectramax i3x. Fluorescence quantum yield was determined using Hamamatsu Quantaurus-QY. All reagents, including salts and solvents, were purchased from Sigma-Aldrich. Light irradiation for photochemical reactions: LED PAR38 lamp (19 W, 3000K).
Compound 3b As depicted in Scheme 3, a solution of IC1 (1.07 g, 6.60 mmol) in MeOH (15 mL) was added dropwise to a stirred solution of compound 3a (1.00 g, 6.60 mmol) and NaOH (266 mg, 6.60 mmol) in MeOH (20 mL). The mixture was stirred at 0° C. for 1 h and monitored by TLC (Hex:EtOAc 80:20). Upon completion, the reaction was quenched with saturated $Na_2S_2O_3$ (25 mL), and stirred for a further 10 min. The mixture was diluted with EtOAc and the organic phase was extracted and washed with saturated $NH_4Cl$. The organic phase was dried over $Na_2SO_4$ and concentrated under reduced pressure. The residue was purified by column chromatography on silica gel (Hex:EtOAc 80:20) which afforded compound 3b as a pale yellow solid (339 mg, 92% yield). $^1HNMR$ (400 MHz, $CDCl_3$) δ 7.73 (s, 1H), 6.80 (s, 1H), 5.72 (s, 1H), 4.43-4.61 (br, 2H), 3.29 (s, 3H), 3.24 (s, 1H), 3.08 (br, 1H), 2.25 (s, 1H), 1.91-1.76 (m, 12H). $^{13}CNMR$ (101 MHz, $CDCl_3$) δ 154.30, 141.20, 138.77, 136.98, 134.89, 134.66, 130.55, 104.65, 85.28, 63.48, 58.04, 39.45, 37.21, 32.80, 29.98, 28.44. MS (ES-): m/z calc. for $C_{19}H_{23}IO_3$: 426.1; found: 425.2 [M-H]⁻.

Compound 3c

As depicted in Scheme 3, to a solution of compound 3b (2.78 g, 6.0 mmol) in EtOAc (20 mL) was added $MnO_2$ (5.22 g, 60.0 mmol). The resulting mixture was heated at 70° C. overnight. Afterward, it was cooled to room temperature and filtered. The filtrate was dried and concentrated under reduced pressure. The residue was purified by column chromatography on silica gel (Hex:EtOAc 85:15) which afforded compound 3c as a pale yellow solid (339 mg, 92% yield). $^1HNMR$ (400 MHz, $CDCl_3$) δ 10.03 (s, 1H), 8.33 (s, 1H), 6.91 (s, 1H), 6.34 (br, 1H), 3.30 (s, 3H), 3.28 (s, 1H), 2.25 (s, 1H), 1.98-1.65 (m, 13H) $^{13}CNMR$ (101 MHz, $CDCl_3$) δ 190.22, 159.30, 142.16, 138.61, 138.17, 135.72, 130.17, 117.28, 86.40, 57.74, 39.27, 39.19, 37.16, 32.93, 30.25, 29.98, 28.37. MS (ES-): m/z calc. for $C_{19}H_{21}IO_3$: 424.0; found: 423.1 [M-H]⁻.

Compound 3d

As depicted in Scheme 3, iodophenol 3c (200 mg, 0.72 mmol), methyl acrylate (200 mg, 0.72 mmol) and $Et_3N$ (200 mg, (072 mmol) were dissolved in anhydrous ACN. Then $Pd(OAc)_2$ (0.05 eq) and $P(o-tol)_3$ (0.01 eq) were added. The flask was sealed and the solution was stirred at 120° C. Reaction was stirred for 2 hours and monitored by TLC (Hex:EtOAc 80:20). Upon completion, reaction mixture was diluted with EtOAc and washed with saturated $NH_4Cl$. The organic phase was dried over $Na_2SO_4$ and concentrated under reduced pressure. The residue was purified by column chromatography on silica gel (Hex:EtOAc 80:20) to afford the corresponding phenol acrylate 3d (339 mg, 92% yield). $^1HNMR$ (400 MHz, $CDCl_3$) δ 10.07 (s, 1H), 8.13 (s, 1H), 8.01 (d, J=16.2 Hz, 1H), 6.91 (s, 1H), 6.71 (d, J=16.2 Hz, 1H), 3.81 (s, 3H), 3.29 (s, 4H), 2.28 (s, 1H), 1.96-1.56 (m, 13H). $^{13}CNMR$ (101 MHz, $CDCl_3$) δ 192.02, 169.12, 161.17, 143.20, 140.08, 138.54, 135.87, 129.57, 127.89, 122.34, 119.52, 118.78, 57.76, 52.36, 39.23, 37.11, 32.96, 31.84, 30.29, 29.95, 28.35, 22.92, 14.39. MS (ES-): m/z calc. for $C_{23}H_{26}O_5$: 382.2; found: 381.1 [M-H]⁻.

Compound 3e

As depicted in Scheme 3, compound 3d (441 mg, 0.95 mmol) and NaOH (114 mg, 2.8 mmol) were dissolved in 5 mL of 4:1 solution $THF:H_2O$. Reaction mixture was stirred at 80° C. and was monitored by RP-HPLC. Upon completion (1 hour), the reaction mixture diluted with EtOAc (100 mL) and was washed with saturated solution of 0.5M HCl (100 mL). The organic layer was separated, washed with brine, dried over $Na_2SO_4$ and evaporated under reduced pressure. The residue was purified by column chromatography on silica gel (Hex:EtOAc 90:10) which afforded compound 3e as a pale yellow solid (339 mg, 92% yield). $^1HNMR$ (400 MHz, $CDCl_3$) δ 9.91 (s, 1H), 7.93 (s, 1H), 7.77 (d, J=16.1 Hz, 1H), 6.70 (s, 1H), 6.48 (d, J=16.1 Hz, 1H), 3.13 (m, 4H), 2.14 (s, 1H), 1.88-1.44 (m, 13H). $^{13}CNMR$ (101 MHz, $CDCl_3$) δ 191.54, 152.69, 140.14, 138.64, 138.32, 136.60, 135.35, 129.48, 129.29, 127.73, 120.32, 120.06, 119.82, 118.27, 57.58, 39.11, 37.10, 32.90, 30.23, 28.34. MS (ES-): m/z calc. for $C_{22}H_{24}O_5$: 368.2; found: 367.2 [M-H]⁻.

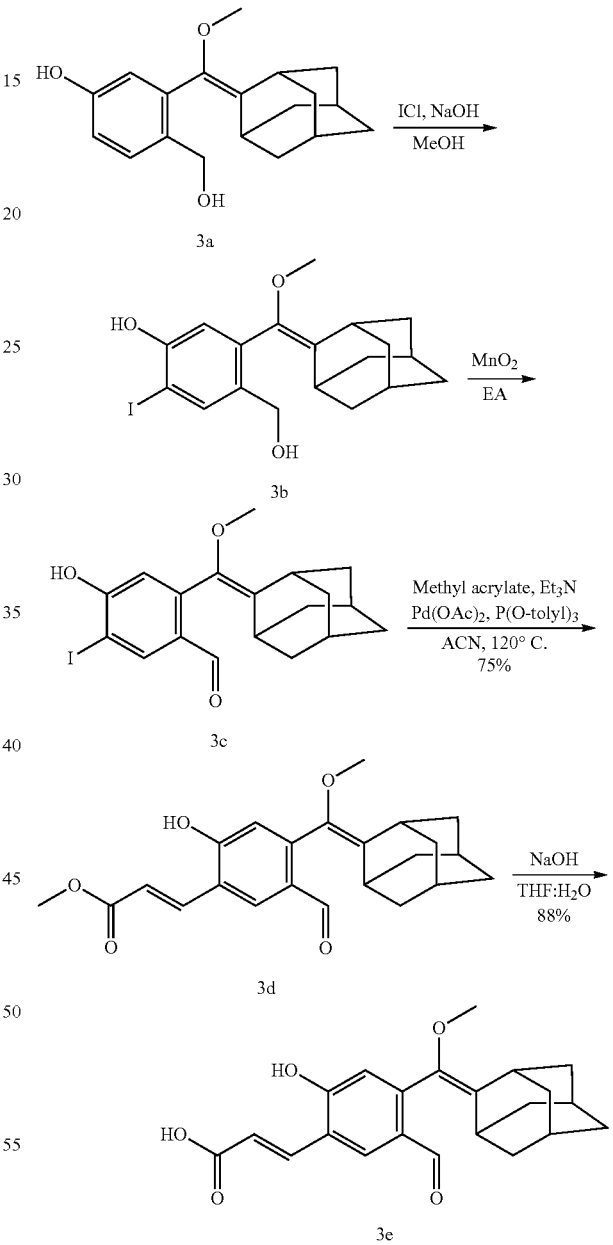

Scheme 3: Synthesis of compound 3e

Compound 3f

As depicted in Scheme 4, to a solution of 2-bromo-5-hydroxybenzaldehyde (200 mg, 0.99 mmol, 1 equiv.) and trimethyl orthoformate (120 μL, 1.1 mmol, 1.1 equiv.) in methanol (5 mL) was added tetrabutylammonium tribromide (3.2 mg, 0.01 mmol, 0.01 equiv.). The homogeneous reaction was left at room temperature, and the progress of the reaction was monitored by TLC (Hex:EtOAc 80:20). After completion, the reaction mixture was poured into water and the product extracted with EtOAc (2×25 mL). The organic layer was separated, dried over anhydrous sodium sulfate, and concentrated. Further purification was achieved by passing through a short column of silica gel, to give 220 mg of compound 5b (yield 89%). $^1$H NMR (400 MHz, CDCl$_3$) δ 7.37 (d, J=8.6 Hz, 1H), 7.11 (d, J=3.1 Hz, 1H), 6.70 (dd, J=8.6, 3.0 Hz, 1H), 5.51 (s, 1H), 3.41 (s, 6H). $^{13}$C NMR (400 MHz, CDCl$_3$) δ 156.03, 138.35, 134.50, 118.40, 116.01, 113.64, 103.97, 55.05. MS (ESI−) m/z 244.9, 246.9 [M-H$^+$] calc. for C$_9$H$_{10}$BrO$_3$ 244.9 246.9.

Mixture of compound 5b (2.2 g, 8.9 mmol, 1 equiv.) and imidazole (1.81 g, 27.3 mmol, 3 equiv.) was dissolved in DCM (20 mL) and then tert-butyl dimethyl silyl chloride (1.62 g, 10.7 mmol, 2 equiv.) was added and the reaction mixture was stirred at room temperature for 1 h. Upon completion, pure water was added to the stirring mixture. The mixture was extracted with DCM (3×60 mL). The organic layer was dried over anhydrous sodium sulfate, solvent was evaporated, and the residue was purified by silica gel column chromatography, to obtain compound 5c, 3.2 g (yield 99%). $^1$H NMR (400 MHz, CDCl$_3$) δ 7.39 (d, J=8.6 Hz, 1H), 7.11 (d, J=3.0 Hz, 1H), 6.70 (dd, J=8.6, 3.0 Hz, 1H), 5.49 (s, 1H), 3.37 (s, 6H), 0.98 (s, 9H), 0.20 (s, 6H). $^{13}$C NMR (400 MHz, CDCl$_3$) δ 156.47, 141.40, 131.82, 124.93, 119.74, 115.57, 103.52, 56.65, 25.66, 18.47.

Trimethyl phosphite (8.6 mL, 84 mmol. 1.4 equiv.) was added to a stirred solution of compound 5c (18 g, 60 mmol, 1 equiv.) in DCM at room temperature. 15 min later, TiCl$_4$ (8.6 mL, 84 mmol. 1.4 equiv.) was added dropwise to the reaction mixture, which was stirred for additional 30 min. The reaction mixture was diluted with DCM (400 mL) and extracted first with saturated solution of NaHCO$_3$ (200 mL) then with brine (200 mL). The combined organic phases were dried over anhydrous Na$_2$SO$_4$. After removal of the solvent, the residue was purified by silica gel flash column chromatography to obtained product 5d as a white solid (18 g, yield 78%). $^1$H NMR (400 MHz, CDCl$_3$) δ 7.36 (dd, J=8.7, 1.0 Hz, 1H), 7.14-7.09 (m, 1H), 6.68 (ddd, J=8.7, 2.9, 1.9 Hz, 1H), 5.01 (d, J=15.7 Hz, 1H), 3.75 (d, J=10.7 Hz, 3H), 3.60 (d, J=10.5 Hz, 3H), 3.31 (s, 3H), 0.93 (d, J=2.9 Hz, 9H), 0.17 (d, J=4.2 Hz, 6H). $^{13}$C NMR (400 MHz, CDCl$_3$) δ 156.17, 135.51, 134.09, 123.12, 122.09, 116.28, 80.02, 59.41, 59.25, 54.44, 54.37, 26.35, 18.94. MS (ESI+) m/z 439.0, 441.1 [M-H$^+$] calc. for C$_{16}$H$_{29}$BrO$_5$PSi 439.0, 441.0.

LDA (12 mL) was added dropwise to the reaction mixture of compound 10 (7 g, 15.9 mmol, 1 equiv.) dissolved in 20 mL dry THF at −78° C. under argon. After stirring of the reaction mixture for 15 min, 2-adamantanone (6.2 g, 20.7 mmol, 1.1 equiv.), dissolved in dry THF (20 mL), was added dropwise to the reaction mixture at −78° C. under argon. The reaction mixture was stirred at room temperature for 2 h. After pouring it into pure water, it was extracted with EtOAc (3×80 mL). The combined organic phases were dried over anhydrous Na$_2$SO$_4$, the solvent was removed, and the residue was purified by silica gel flash column chromatography to give product 5e (5.5 g, yield 75%). $^1$H NMR (400 MHz, CDCl$_3$) δ 7.41 (d, J=8.6 Hz, 1H), 6.72 (d, J=2.9 Hz, 1H), 6.67 (dd, J=8.6, 2.9 Hz, 1H), 3.30 (s, 3H), 3.25 (m, 1H), 2.35 (m, 1H), 1.93-1.69 (m, 12H), 0.96 (s, 9H), 0.17 (s, 6H). $^{13}$C NMR (400 MHz, CDCl$_3$) δ 155.32, 142.19, 137.96, 134.07, 131.00, 124.72, 122.19, 117.07, 57.47, 54.13, 39.88, 39.75, 39.39, 39.12, 37.89, 33.54, 30.19, 29.17, 29.01, 26.37, 18.97. MS (ESI+) m/z 463.1, 465.1 [M-H$^+$] calc. for C$_{24}$H$_{36}$BrO$_2$Si 463.1, 465.1.

Compound 5e (4.5 g, 9.7 mmol, 1 equiv.) was dissolved in THF (20 mL) under N$_2$ atmosphere. The solution was cooled to −78° C. and n-BuLi (7.8 mL, 2.5 M in Hex) was added. After 15 min of stirring, DMF (2.7 mL) was added. The reaction mixture was heated to room temperature with stirring for 30 min and monitored by TLC. After completion, saturated solution of ammonium chloride (5 mL) was added. The mixture was extracted with EtOAc (3×30 mL). The combined organic layer was washed with brine (25 mL), dried over Na$_2$SO$_4$ and evaporated under reduced pressure, the product purified by column chromatography to give 3 g of yellow solid (72% yield). $^1$H NMR (400 MHz, CDCl$_3$) δ 9.99 (s, 1H), 7.80 (dd, J=8.6, 0.8 Hz, 1H), 6.85-6.77 (m, 1H), 6.68 (dd, J=2.3, 0.9 Hz, 1H), 3.21 (m, 4H), 2.17 (s, 1H), 1.91-1.57 (m, 12H). $^{13}$C NMR (400 MHz, CDCl$_3$) δ 192.52, 162.82, 142.83, 139.36, 134.83, 130.46, 128.35, 118.53, 116.65, 57.94, 39.64, 37.69, 33.31, 30.62, 28.89, 26.39. MS (ESI−) m/z 297.2 [M-H$^+$] calc. for C$_{19}$H$_{21}$O$_3$ 297.2.

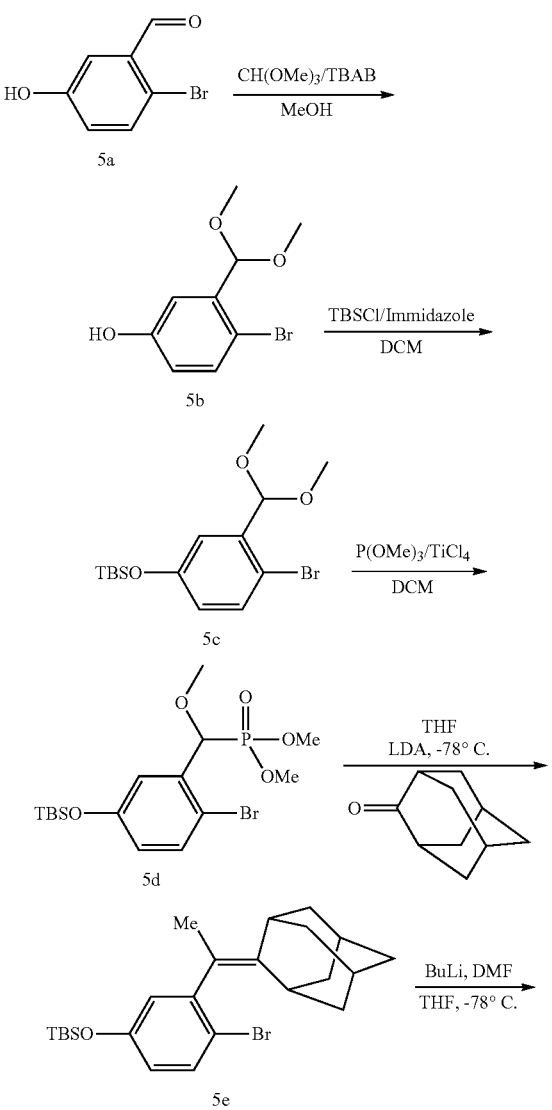

Scheme 4: Synthesis of compound 3f

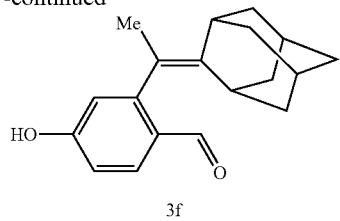

3f

Luminophore 1

As depicted in Scheme 5, compound 3f (1 eq), piperidine (1.25 eq) and DCMC (1.05 eq) were dissolved in 3 mL of ACN. Reaction mixture was stirred at reflux for 1 hour and the reaction was monitored by RP-HPLC. Upon completion, the reaction mixture diluted with EtOAc (100 mL) and was washed with a solution of 0.5M HCl (100 mL). The organic layer was separated, washed with brine, dried over $Na_2SO_4$ and evaporated under reduced pressure. The crude orange residue and few milligrams of methylene blue were dissolved in 20 mL of DCM. Oxygen was bubbled through the solution while irradiating with yellow light. The reaction was monitored by RP-HPLC. Upon completion, the solvent was concentrated under reduced pressure and the product was purified by preparative RP-HPLC (gradient of ACN in water). The product Luminophore 1 was obtained as orange solid (63% yield).

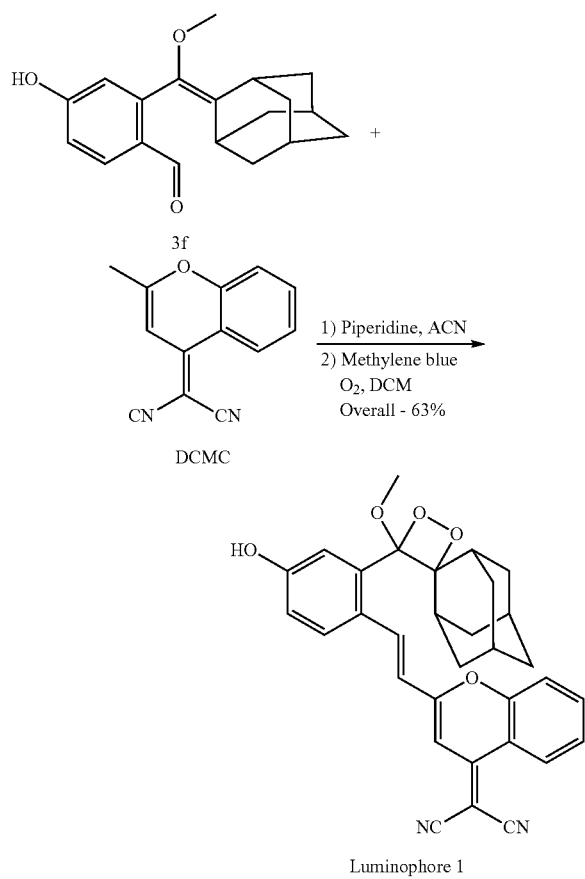

Scheme 5: Synthesis of Luminophore 1

Luminophore 2

As depicted in Scheme 6, compound 3e (1 eq), piperidine (1.25 eq) and DCMC (1.05 eq) were dissolved in 3 mL of THF. Reaction mixture was stirred at reflux for 1 hour and the reaction was monitored by RP-HPLC. Upon completion, the reaction mixture diluted with EtOAc (100 mL) and was washed with a solution of 0.5M HCl (100 mL). The organic layer was separated, washed with brine, dried over $Na_2SO_4$ and evaporated under reduced pressure. The crude orange residue and few milligrams of methylene blue were dissolved in 20 mL of DCM. Oxygen was bubbled through the solution while irradiating with yellow light. The reaction was monitored by RP-HPLC. Upon completion, the solvent was concentrated under reduced pressure and the product was purified by preparative RP-HPLC (gradient of ACN in water). Luminophore 2 was obtained as orange solid (76% yield).

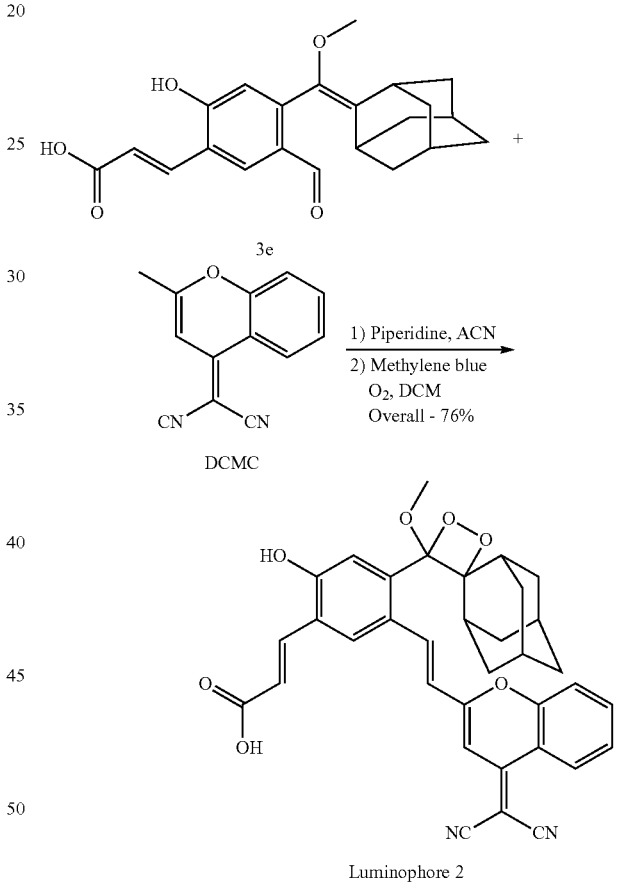

Scheme 6: Synthesis of Luminophore 2

Luminophore 3

As depicted in Scheme 7, compound 3e (441 mg, 0.95 mmol), $NH_4OAc$ (114 mg, 2.8 mmol) and TCF were dissolved in 3 mL of THF. Reaction mixture was stirred at reflux for 1 hour and the reaction was monitored by RP-HPLC. Upon completion, the reaction mixture diluted with EtOAc (100 mL) and was washed with a solution of 0.5M HCl (100 mL). The organic layer was separated, washed with brine, dried over $Na_2SO_4$ and evaporated under reduced pressure. The crude orange residue and few milligrams of methylene blue were dissolved in 20 mL of DCM. Oxygen was bubbled through the solution while irradiating with yellow light. The reaction was monitored by RP-HPLC.

Upon completion, the solvent was concentrated under reduced pressure and the product was purified by preparative RP-HPLC (gradient of ACN in water). The product Luminophore 3 was obtained as orange solid (201 mg, 64% yield).

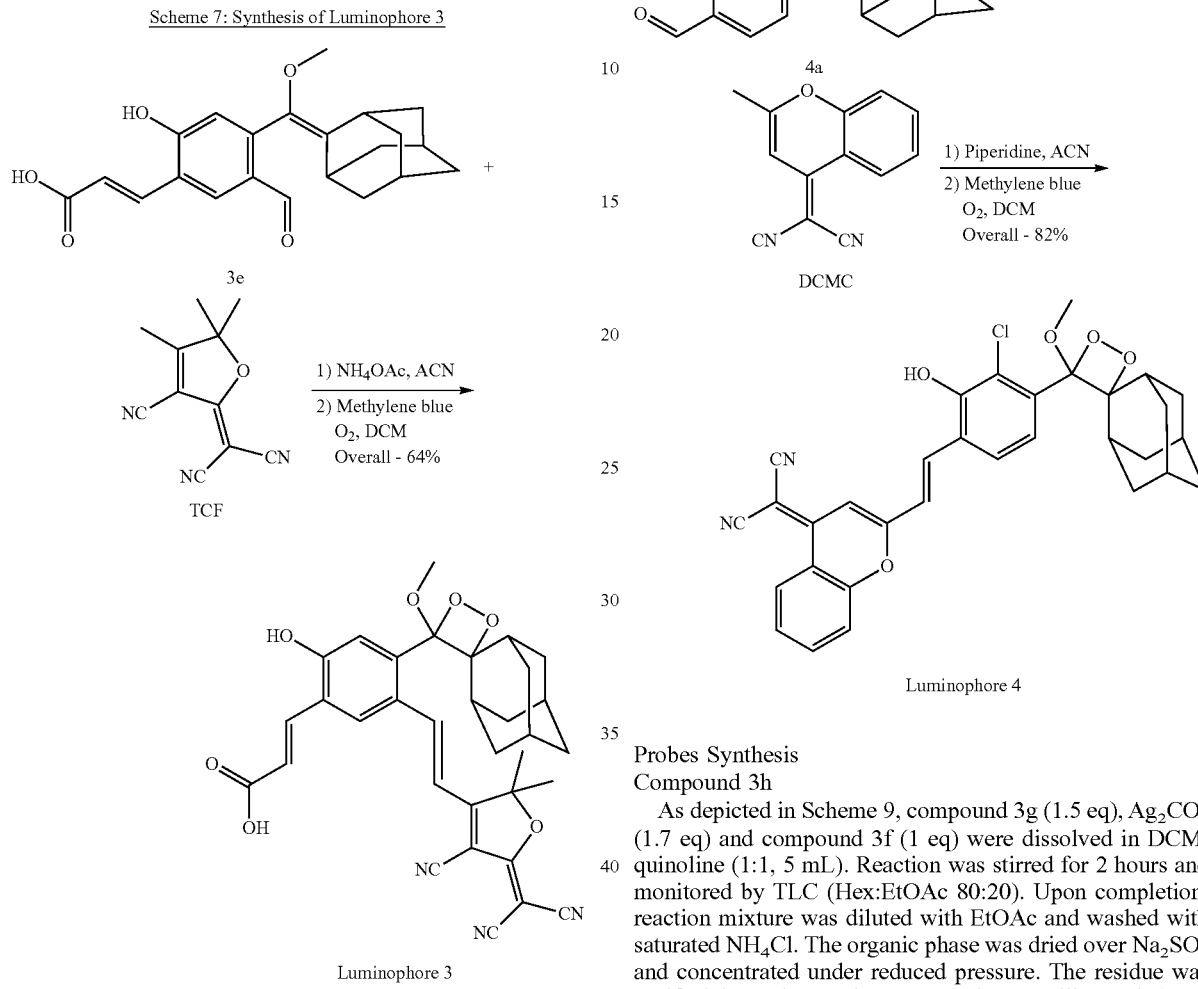

Luminophore 3

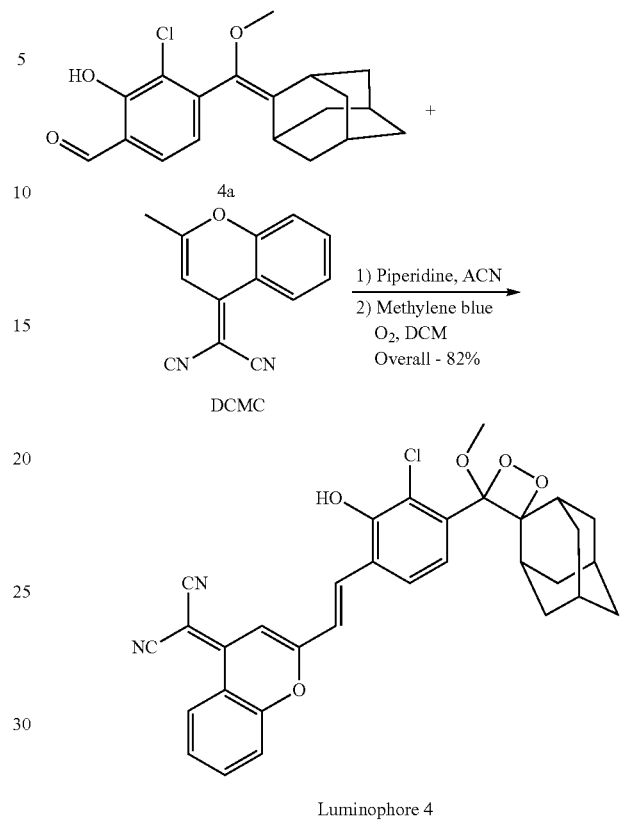

Luminophore 4

Luminophore 4

As depicted in Scheme 8, the corresponding phenol aldehyde (1 eq), piperidine (1.25 eq) and DCMC (1.05 eq) were dissolved in 3 mL of THF. Reaction mixture was stirred at reflux for 1 hour and the reaction was monitored by RP-HPLC. Upon completion, the reaction mixture diluted with EtOAc (100 mL) and was washed with a solution of 0.5M HCl (100 mL). The organic layer was separated, washed with brine, dried over $Na_2SO_4$ and evaporated under reduced pressure. The crude orange residue and few milligrams of methylene blue were dissolved in 20 mL of DCM. Oxygen was bubbled through the solution while irradiating with yellow light. The reaction was monitored by RP-HPLC. Upon completion, the solvent was concentrated under reduced pressure and the product was purified by preparative RP-HPLC (gradient of ACN in water). Luminophore 4 was obtained as orange solid (82% yield).

Probes Synthesis

Compound 3h

As depicted in Scheme 9, compound 3g (1.5 eq), $Ag_2CO_3$ (1.7 eq) and compound 3f (1 eq) were dissolved in DCM: quinoline (1:1, 5 mL). Reaction was stirred for 2 hours and monitored by TLC (Hex:EtOAc 80:20). Upon completion, reaction mixture was diluted with EtOAc and washed with saturated $NH_4Cl$. The organic phase was dried over $Na_2SO_4$ and concentrated under reduced pressure. The residue was purified by column chromatography on silica gel (Hex: EtOAc 50:50) to afford compound 3h (71% yield).

Probe 1a

As depicted in Scheme 9, compound 3h (1 eq), piperidine (1.25 eq) and DCMC (1.05 eq) were dissolved in 3 mL of THF. Reaction mixture was stirred at reflux for 1 hour and the reaction was monitored by RP-HPLC. Upon completion, the reaction mixture diluted with EtOAc (100 mL) and was washed with saturated solution of 0.5M HCl (100 mL). The organic layer was separated, washed with brine, dried over $Na_2SO_4$ and evaporated under reduced pressure. the crude residue was added NaOH (4 eq) and 5 mL of 4:1 solution THF:$H_2O$. The reaction mixture was stirred at 70° C. and monitored by RP-HPLC. Upon completion (1 hour), the reaction mixture diluted with EtOAc (100 mL) and was washed with saturated solution of 0.5M HCl (100 mL). The organic layer was separated, washed with brine, dried over $Na_2SO_4$ and evaporated under reduced pressure. The crude orange residue and few milligrams of methylene blue were dissolved in 20 mL of DCM. Oxygen was bubbled through the solution while irradiating with yellow light. The reaction was monitored by RP-HPLC. Upon completion, the solvent was concentrated under reduced pressure and the product was purified by preparative RP-HPLC (gradient of ACN in water). The product, Probe 1a, was obtained as orange solid (201 mg, 47% yield).

Compound 3j

As depicted in Scheme 10, enol ether 3d (500 mg, 1.41 mmol) and triethylamine (0.49 ml, 3.5 mmol) were dissolved in 5 mL of DCM and cooled to 0° C. Trifluoromethanesulfonic anhydride (0.29 mL, 1.7 mmol) was added. Reaction mixture was stirred for 30 minutes and monitored by TLC. Upon completion, reaction mixture was diluted with DCM (100 mL) and washed with brine (100 mL). Organic phase was dried over $Na_2SO_4$ and concentrated under reduced pressure. Purification by column chromatography (Hex:EtOAc 80:20) afforded compound 3j as a yellow viscos oil (562 mg, 86% yield). $^1$HNMR (400 MHz, $CDCl_3$) δ 10.22 (s, 1H), 8.27 (s, 1H), 7.85 (d, J=16.0 Hz, 1H), 7.30 (s, 1H), 6.64 (d, J=16.0 Hz, 1H), 3.84 (s, 3H), 3.32 (s, 4H), 2.31 (s, 1H), 2.11-1.62 (m, 13H). $^{13}$CNMR (101 MHz, $CDCl_3$) δ 190.40, 181.58, 142.12, 138.77, 134.75, 133.44, 128.01, 125.14, 123.51, 93.50, 58.54, 52.27, 39.04, 36.29, 32.96, 30.18, 27.14. MS (ES+): m/z calc. for $C_{24}H_{25}F_3O_7S$: 514.1; found: 537.2 [M+Na]$^+$.

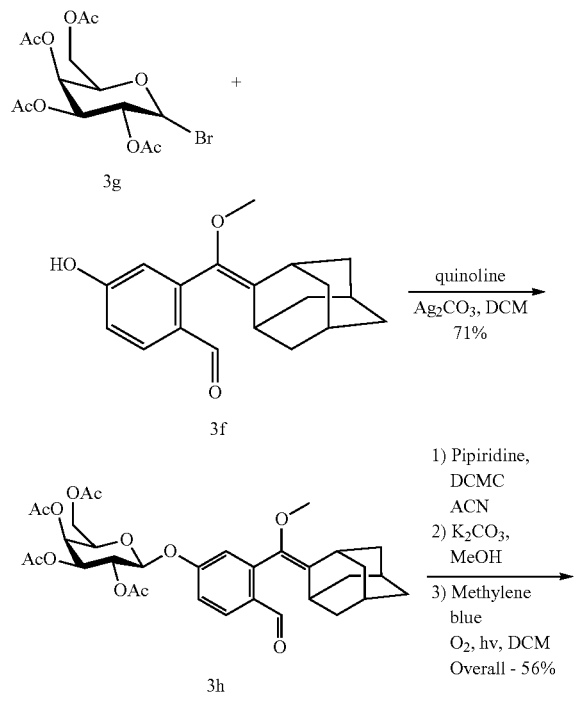

Scheme 9: Synthesis of Probe 1a

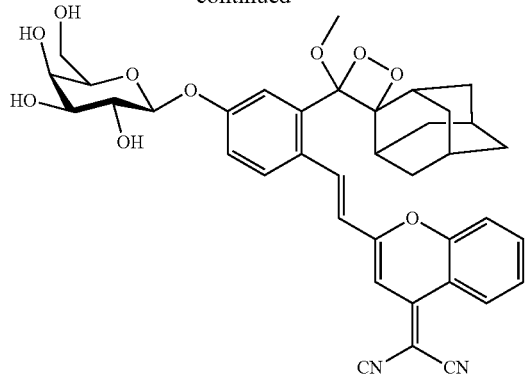

Probe 1a

Compound 3k

As depicted in Scheme 10, compound 3j (562 mg, 1.16 mmol), bis(pinacolato)diboron (589 mg, 2.32 mmol), potassium acetate (341 mg, 3.48 mmol) and [1,1'-bis(diphenylphosphino) ferrocene] dichloropalladium(II) (170 mg, 0.23 mmol) were dissolved in 20 mL of dry dioxane and stirred for 1 hour at 120° C. under argon. Reaction was monitored by RP-HPLC. Upon completion, reaction mixture was diluted with EtOAc (100 mL) and washed with brine. Organic phase was dried over $Na_2SO_4$ and concentrated under reduced pressure. Then, to the crude residue was added (441 mg, 0.95 mmol), NaOH (114 mg, 2.8 mmol) and 5 mL of 4:1 solution $THF:H_2O$. The reaction mixture was stirred at 70° C. and monitored by RP-HPLC. Upon completion (1 hour), the reaction mixture diluted with EtOAc (100 mL) and was washed with saturated solution of 0.5M HCl (100 mL). The organic layer was separated, washed with brine, dried over $Na_2SO_4$ and evaporated under reduced pressure. The residue was purified by column chromatography on silica gel (Hex:EtOAc 50:50) which afforded compound 3k as a solid (339 mg, 63% yield). $^1$HNMR (400 MHz, $CDCl_3$) δ 10.25 (s, 1H), 8.51 (d, J=15.9 Hz, 1H), 8.19 (s, 1H), 7.75 (s, 1H), 6.47 (d, J=15.9 Hz, 1H), 3.31 (s, 1H), 3.26 (s, 3H), 2.20 (s, 1H), 2.01-1.64 (m, 13H), 1.36 (s, 12H). $^{13}$CNMR (101 MHz, $CDCl_3$) δ 192.63, 170.44, 145.57, 140.11, 139.05, 138.89, 138.57, 136.53, 136.07, 124.27, 120.50, 84.77, 77.52, 77.21, 76.89, 75.40, 57.54, 39.03, 37.08, 32.81, 32.00, 30.40, 30.22, 29.77, 29.43, 28.24, 24.90, 24.82, 22.76, 14.19.

Scheme 10: Synthesis of Probe 2a

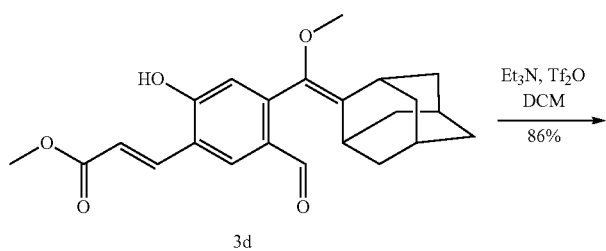

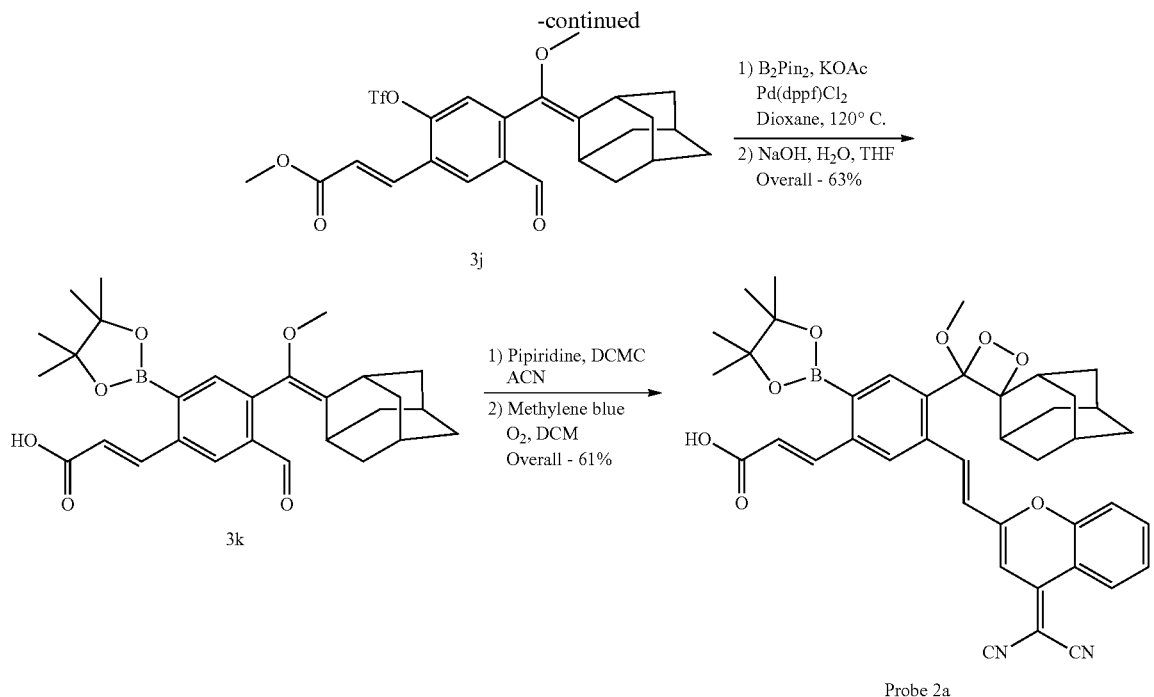

Probe 2a

As depicted in Scheme 10, compound 3k (441 mg, 0.95) mmol piperidine (1.25 eq) and DCMC (1.05 eq) were dissolved in 3 mL of THF. Reaction mixture was stirred at reflux for 1 hour and the reaction was monitored by RP-HPLC. Upon completion, the reaction mixture diluted with EtOAc (100 mL) and was washed with saturated solution of 0.5M HCl (100 mL). The organic layer was separated, washed with brine, dried over $Na_2SO_4$ and evaporated under reduced pressure. The crude orange residue and few milligrams of methylene blue were dissolved in 20 mL of DCM. Oxygen was bubbled through the solution while irradiating with yellow light. The reaction was monitored by RP-HPLC. Upon completion, the solvent was concentrated under reduced pressure and the product was purified by preparative RP-HPLC (gradient of ACN in water). The product was obtained as a orange solid (201 mg, 47% yield). $^1$HNMR (400 MHz, $CDCl_3$) δ 8.81 (d, J=8.4 Hz, 1H), 8.38 (d, J=15.5 Hz, 1H), 7.69 (m, 2H), 7.41 (m, 2H), 7.12 (s, 1H), 6.79 (s, 1H), 6.65 (d, J=15.7 Hz, 1H), 3.29 (s, 1H), 3.08 (s, 3H), 2.12 (s, 1H), 2.03-1.30 (m, 12H), 1.17 (s, 12H).

Compound 3l

As depicted in Scheme 11, compound 3d (1 eq) was dissolved in 1 mL dry DMF and cooled to 0° C. $K_2CO_3$ (2 eq) was added and the solution stirred at 0° C. for 10 minutes, before iodomethane (3 eq) was added. The reaction mixture stirred for 30 minutes at room temperature and monitored by TLC (Hex:EtOAc 50:50). Upon completion (~1 hour) the reaction mixture was diluted with EtOAc (100 mL) and washed with brine (100 mL). The organic phase was dried over $Na_2SO_4$ and concentrated under reduced pressure. To the crude residue was added NaOH (4 eq) and 5 mL of 4:1 solution $THF:H_2O$. Reaction mixture was stirred at 70° C. and monitored by RP-HPLC. Upon completion (1 hour), the reaction mixture diluted with EtOAc (100 mL) and was washed with a solution of 0.5M HCl (100 mL). The organic layer was separated, washed with brine, dried over $Na_2SO_4$ and evaporated under reduced pressure. The residue was purified by column chromatography on silica gel (Hex:EtOAc 90:10) which afforded compound 3l as a solid (73% yield). $^1$HNMR (400 MHz, $CDCl_3$) δ10.11 (s, 1H), 8.12 (s, 1H), 7.94 (d, J=16.2 Hz, 1H), 6.80 (s, 1H), 6.58 (d, J=16.1 Hz, 1H), 3.94 (s, 3H), 3.29 (s, 4H), 2.22 (s, 1H), 2.04-1.56 (m, 13H). $^{13}$CNMR (101 MHz, $CDCl_3$) δ191.39, 175.38, 162.18, 143.26, 139.51, 138.47, 135.91, 128.55, 128.40, 124.05, 120.65, 113.20, 57.72, 56.32, 39.15, 37.13, 33.01, 30.33, 29.94, 28.34. MS (ES+): m/z calc. for $C_{23}H_{26}O_5$: 382.2; found: 405.2 $[M+Na]^+$.

Scheme 11: Synthesis of Proble 2b

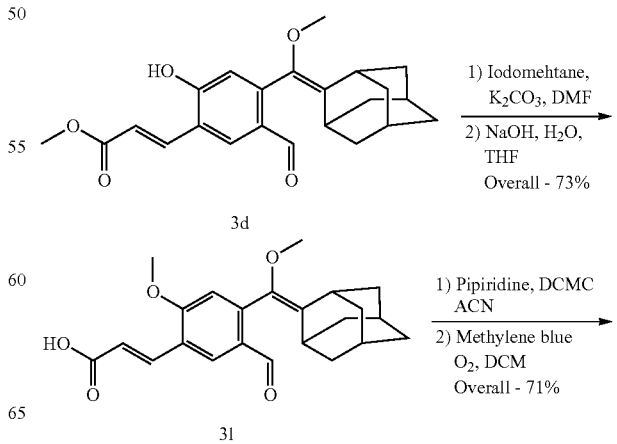

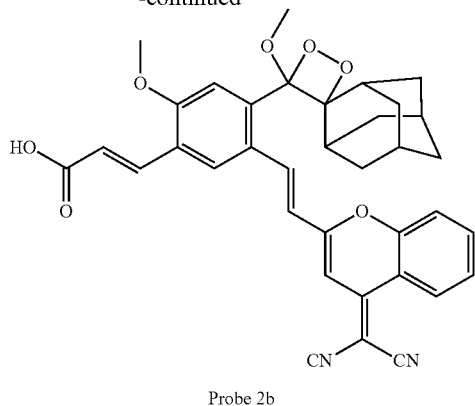

Probe 2b

Probe 2b

As depicted in Scheme 11, compound 3l (1 eq), piperidine (1.25 eq) and DCMC (1.05 eq) were dissolved in 3 mL of ACN. Reaction mixture was stirred at reflux for 1 hour and the reaction was monitored by RP-HPLC. Upon completion, the reaction mixture diluted with EtOAc (100 mL) and was washed with saturated solution of 0.5M HCl (100 mL). The organic layer was separated, washed with brine, dried over $Na_2SO_4$ and evaporated under reduced pressure. The crude orange residue and few milligrams of methylene blue were dissolved in 20 mL of DCM. Oxygen was bubbled through the solution while irradiating with yellow light. The reaction was monitored by RP-HPLC.

Upon completion, the solvent was concentrated under reduced pressure and the product was purified by preparative RP-HPLC (gradient of ACN in water). The product was obtained as an orange solid (71% yield).

Compound 3n

As depicted in Scheme 12, compound 3c (100 mg, 0.24 mmol), was dissolved in 1 mL DMF. $K_2CO_3$ (40 mg, 0.28 mmol) was added and the solution stirred at 0° C. for 10 minutes, before compound 3m (100 mg, 0.24 mmol), was added. The reaction mixture stirred for 30 minutes at room temperature and monitored by TLC (Hex:EtOAc 50:50). After completion, the reaction mixture diluted with EtOAc (100 ml) and was washed with saturated $NH_4Cl$ (100 ml). The organic layer was separated, washed with brine, dried over $Na_2SO_4$ and evaporated under reduced pressure. The crude product was purified by column chromatography on silica gel (Hex:EtOAc 50:50). The product was obtained as an yellow solid (133 mg, 82% yield).

Compound 3p

As depicted in Scheme 12, compound 3n (100 mg, 0.15 mmol), compound 3o (113 mg, 0.45 mmol) and $Et_3N$ (62 μL, 0.45 mmol) were dissolved in anhydrous ACN. Then $Pd(OAc)_2$ (2 mg, 0.007 mmol) and $P(o-tol)_3$ (4 mg, 0.015 mmol) were added. The flask was sealed and the solution was stirred at 120° C. Reaction was stirred for 2 hours and monitored by TLC (Hex:EtOAc 80:20). Upon completion, reaction mixture was diluted with EtOAc and washed with saturated $NH_4Cl$. The organic phase was dried over $Na_2SO_4$ and concentrated under reduced pressure. The residue was purified by column chromatography on silica gel (Hex: EtOAc 80:20) to afford the compound 3p (94 mg, 79% yield).

Probe 3a

As depicted in Scheme 12, compound 3p (50 mg, 0.06 mmol), $NH_4OAc$ (10 mg, 0.13 mmol) and TCF (16 mg, 0.08 mmol) were dissolved in 3 mL of THF. Reaction mixture was stirred at reflux for 1 hour and the reaction was monitored by RP-HPLC. Upon completion, the reaction mixture diluted with EtOAc (100 mL) and was washed with a solution of 0.5M HCl (100 mL). The organic layer was separated, washed with brine, dried over $Na_2SO_4$ and evaporated under reduced pressure. The crude orange residue and few milligrams of methylene blue were dissolved in 20 mL of DCM. Oxygen was bubbled through the solution while irradiating with yellow light. The reaction was monitored by RP-HPLC. Upon completion, the solvent was concentrated under reduced pressure and the product was purified by preparative RP-HPLC (gradient of ACN in water). The product was obtained as orange solid (46 mg, 73% yield).

Scheme 12: Synthesis of Probe 3a

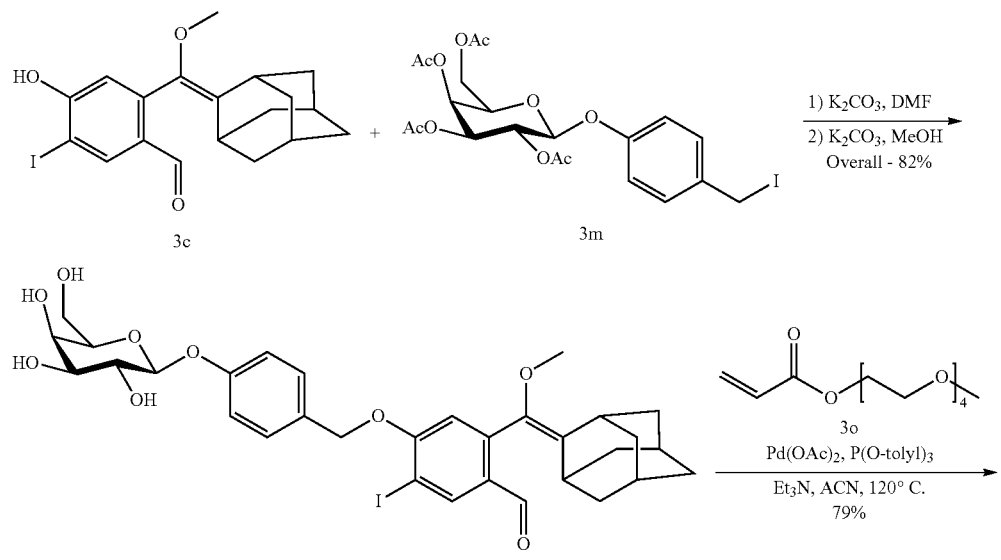

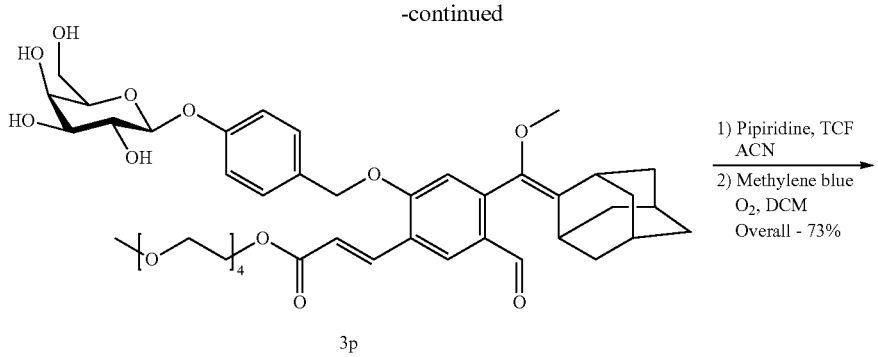

3p

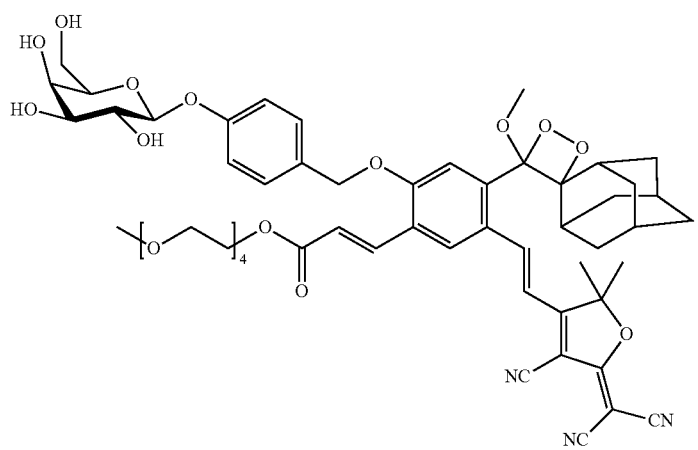

Probe 3a

Results and Discussion

In order to design luminophores with NIR emission we needed to further extend the conjugated electron π system of the modified Schaap's 1,2-dioxetane probe disclosed in the International Publication No. WO 2017/130191 in such manner that produces a NIR donor-acceptor pair. In recent years, much attention has been given to NIR probes that are based on the design of a phenol-donor and a DCMC electron acceptor. Such DCMC based push-pull systems are known to produce NIR emissive species with high $\Phi_{FL}$ and good photostability. Therefore, we have included such electron acceptors in the design of NIR luminophores 1 and 2. Deprotonation of such luminophore initiates a chemiexcitation process to generate a NIR fluorophore in its excited state. The latter will decay to its ground state while releasing a NIR photon (Scheme 13). The structural design of Luminophores 1 and 2 is composed of phenol donor and a DCMC acceptor, whereas Luminophore 2 was introduced with an acrylic-acid substituent that extends the π conjugated system and increases the liminophore's solubility under physiological conditions.

Scheme 13: General activation pathway of Schaap's 1,2-dioxetanes based NIR luminophores

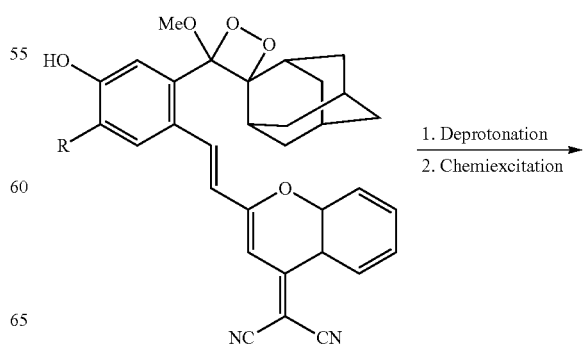

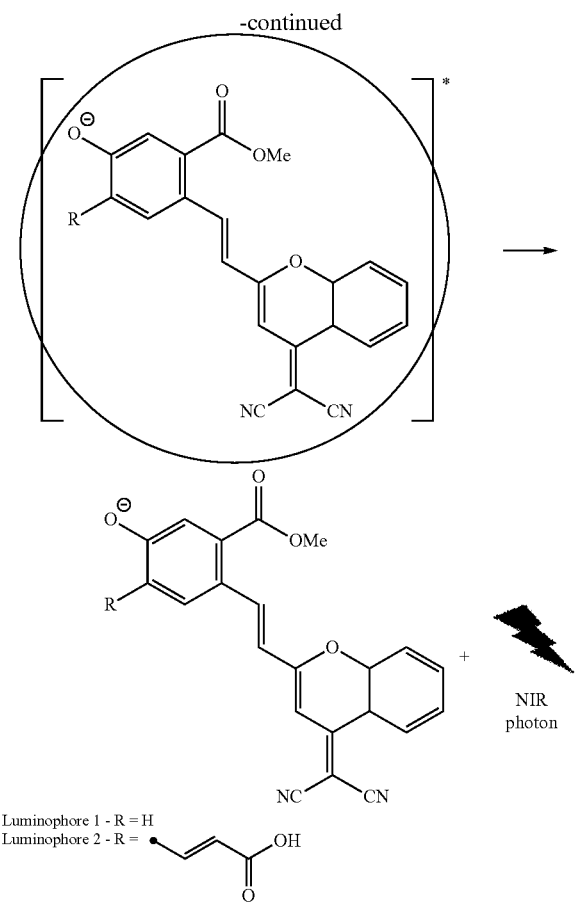

Luminophore 1 - R = H
Luminophore 2 - R = ⦁⎯CH=CH⎯C(=O)⎯OH

Next, we incubated our luminophores under physiological conditions and evaluated their properties. The chemiluminescence emission spectra of luminophores 1 and 2 were found to be in the NIR region with a maximal emission at 660 and 690 nm respectively. As expected, the chemiluminescence emission spectra correlate with the fluorescence spectra of their corresponding decomposition benzoate esters products. Both luminophores display a chemiluminescence kinetic profile in which Luminophore 2 shows faster kinetic profile ($T_{1/2}$=53 minutes) compared to that of Luminophore 1 ($T_{1/2}$=178 minutes). This difference is attributed to the reduced pKa of Luminophore 2, which accelerate the generation of enriched phenolate population that spontaneously undergoes the chemiexcitation process. The chemiluminescence efficiency of Luminophores 1 and 2 was calculated to be 0.82% and 1.12% respectively. The spectral properties of 1 and 2, as well as of luminophores 3 and 4, are summarized in Table 4. These outstanding results encouraged us to investigate the imaging features of our NIR luminophores to serve as a reporter both in-vitro and in-vivo bioassays.

TABLE 4

Molecular structures and chemiluminescence properties of NIR luminophores 1-4

| Luminophore | λ max$_{CL}$ [nm] | $T_{1/2}$ [min] | $\Phi_{CL(\%)}$ | pKa |
|---|---|---|---|---|
| 1 | 660 | 178 | 0.82 | ~8.8 |
| 2 | 690 | 53 | 1.12 | 7.35 |
| 3 | 670 | 30 | 0.70 | 7.71 |
| 4 | 730 | 10 | 0.95 | 6.72 |

Chemiluminescent turn-ON probes can be generated by simply masking the luminophores' phenol with a specific protecting group. First, we have used this strategy to design and synthesize Probe 1a which is capable of monitoring the activity of β-galactosidase. This enzyme is commonly used as a gene reporter, has important physiological roles and can function as a cancer biomarker. Hence, we have synthesized Probe 1a with a β-galactosidase substrate as the responsive protecting group.

Figure 1A:
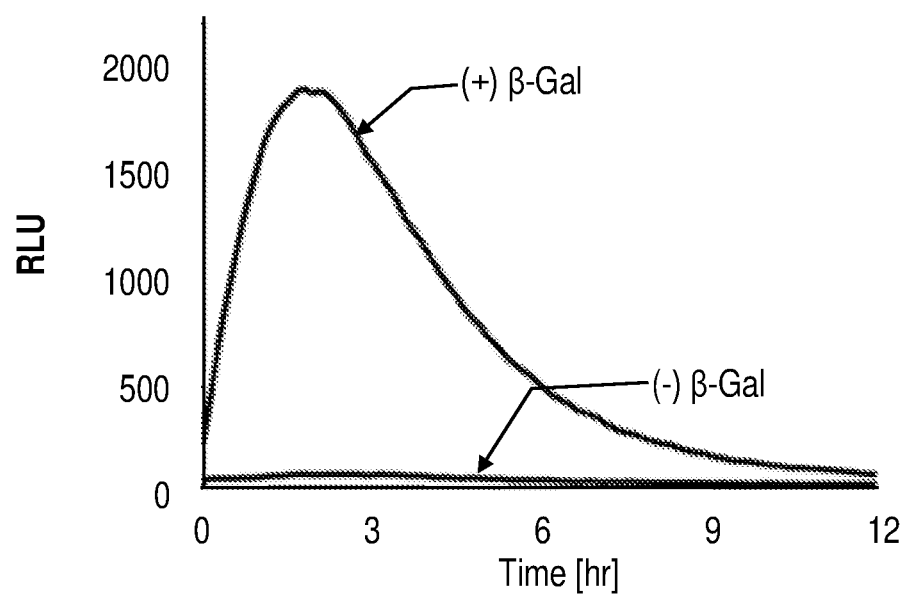
FIGS. 1A-1C show the chemiluminescence kinetic profiles of probes 1a [10 µM] in PBS, pH 7.4, in the presence and absence of 1.5 units/mL β-galactosidase at 37° C. (1A)
Figure 1B:
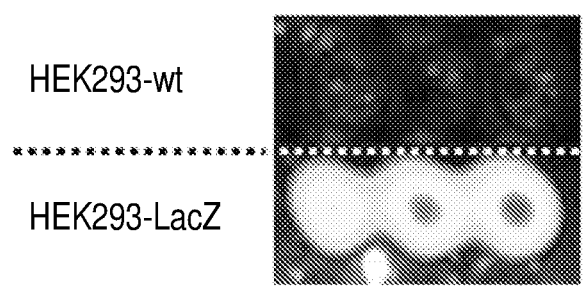
Figure 1C:
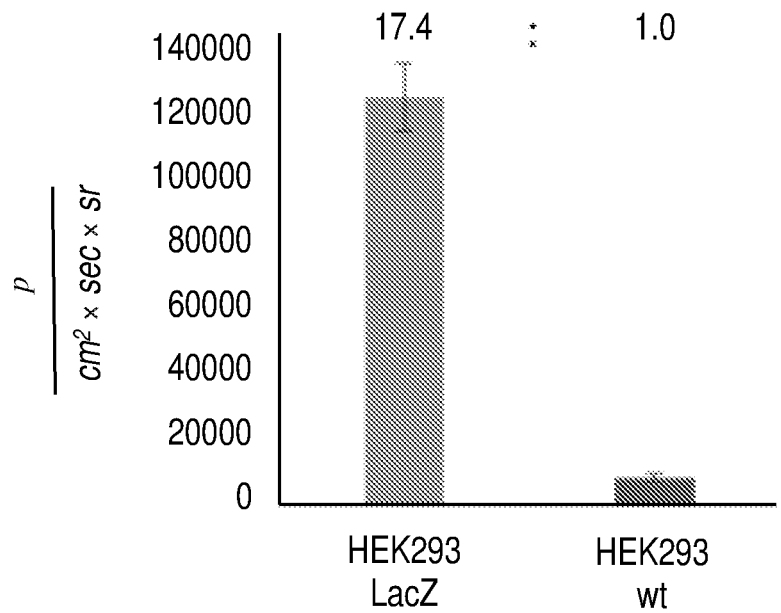

The spectral performance of Probe 1a was evaluated by measuring the chemiluminescent signal over time while its incubation took place under physiological conditions in the presence and absence of β-galactosidase (FIG. 1A). Probe 1a displayed a typical chemiluminescent kinetic profile with a signal-to-noise ratio of 17. The emission spectra of 1a overlaps with its parent Luminophore 1 as expected. Next, we investigated the feasibility of Probe 1a to image the over expression of endogenous β-galactosidase in HEK293 cells transfected with the LacZ gene. We incubated Probe 1a with HEK293-LacZ and HEK293-wt cells. Remarkably, Probe 1a generated intense chemiluminescent signal when incubated with HEK293-LacZ cell while negligible chemiluminescent signal was observed for HEK293-wt cell (FIG. 1B). The chemiluminescence signal was quantified as depicted in FIG. 1C. The ratio between the signal intensities of the transfected cells to that of the wild type cells was found to be 14, thus we have demonstrated the ability of Probe 1a to image at real-time β-galactosidase activity in living cell using a chemiluminescent imaging technique.

The study in which the feasibility of Probe 1a to image the over expression of endogenous β-galactosidase in HEK293 cells transfected with the LacZ gene was repeated using Probe 3a, corresponding to Luminophore 3 wherein the phenol is masked with a β-galactosidase substrate as the responsive protecting group, and a short polyethylene-glycol ester is introduced instead of the carbolic acid residue, considering that cell permeability is reduced by negatively charged species. Probe 3a displayed a typical chemiluminescent kinetic profile with signal-to-noise ratio of 43, wherein the emission spectra of 3a overlaps with its parent Luminophore 3 as expected (FIG. 2).

In order to investigate the feasibility of Probe 3a to monitor the enzymatic activity of β-galactosidase in vitro, the probe [1 μM] was incubated for 30 minutes with transfected HEK293-LacZ cell that overexpress the enzyme β-galactosidase, and under the same conditions with HEK293-wt cell as a control. The chemiluminescent signal was collected for 4 hours from the samples and quantified as depicts in FIG. 3. Probe 3a generated intense chemiluminescent signal when incubated with HEK293-LacZ cell while unneglectable chemiluminescent signal was observed for HEK293-wt cell. The signal ratio between the transfected cells to the wild type was found to be 17, demonstrating the ability of Probe 3a to image at real-time β-galactosidase activity in living cell using a chemiluminescent imaging technique.

To further demonstrate the ability of our NIR luminophores to serve as reporters for bioimaging, we used Probe 2a that was designed for the detection of hydrogen peroxide ($H_2O_2$) in living targets. As a secondary metabolite, $H_2O_2$ is tightly linked to diverse cellular processes such as growth, proliferation, differentiation, and migration. Therefore, there is an urgent demand to develop new methods for real-time monitoring of $H_2O_2$ in living organisms. Our strategy to construct an $H_2O_2$ responsive probe is to exchange the phenol-donor of Luminophore 2 with an aryl-boronate moiety. The aryl-boronate can undergo oxidation reaction exclusively with $H_2O_2$ to give the corresponding phenol with high specificity. Therefore, Probe 2a was designed based on the structure of Luminophore 2, whereas the phenol was replaced by an aryl-boronate ester.

At first, we wanted evaluated the ability of Probe 2a to detect $H_2O_2$, therefore we incubated Probe 2a in the presence and absence of $H_2O_2$ and monitored the emitted light. Probe 2a displayed a typical chemiluminescent kinetic profile with signal-to-noise ratio of 57, and the chemiluminescence spectra showed full correlation to its parent Luminophore 2. These results suggest that Probe 2a is indeed capable monitoring $H_2O_2$ in real-time.

Since we established that our luminophores can serve as chemiluminescence reporter for in-vitro imaging we wanted to test their ability to image a whole animal. We tested the ability of Probe 2a to detect endogenous $H_2O_2$ by using a mouse model peritonitis that was induced by intraperitoneal injection of lipopolysaccharide (LPS). In order to prove that Probe 2a is indeed activated by the reaction of endogenous $H_2O_2$ with the aryl-boronate moiety we synthesized Probe 2b, wherein the phenol is masked by a methyl that cannot be removed by $H_2O_2$. Three groups of mice were applied: (A) mice that were treated with LPS followed by the injection of probe 2a; (B) mice that were treated with LPS followed by the injection of Probe 2b; and (C) mice that were treated with vehicle control (PBS 7.4) followed by the injection of Probe 2a.

Right after the probes' injections, an efficient chemiluminescence signal was observed from the mice in group A compared with that of groups B and C. After 1 minute, a ratio of 19 was observed comparing the signal intensities of LPS treated and non-LPS treated mice which were injected with Probe 2a (groups A and C). The evolved chemiluminescence from the LPS treated mice, which were injected with Probes 2a and 2b (groups A and B), revealed a signal ratio of 45 (FIG. 4).

The high signal ratio that was observed implies that Probe 2a can serve as a diagnostic tool for real-time imaging with potential to identify inflammatory diseases at early stages. Such results emphasis the ability of Luminophore 2 to serve as a reporter for chemiluminescence imaging in biomolecular systems.

In summary, we have developed NIR chemiluminescent luminophores that emit light under physiological conditions with high efficiency. We measured their optical properties and confirmed that they emit NIR light by simple deprotonation that initiate the chemiluminescence process. Since these luminophores are based on Schaap's 1,2-dioxetanes their triggering event can be modified by exchanging the phenol with an appropriate protecting group. This was demonstrated by the design and synthesis of chemiluminescent NIR probes suitable for detecting $H_2O_2$ and monitoring the enzymatic activity of β-galactosidase, which are important biological markers related to many inflammations and diseases. One of these probes successfully imaged in-vivo the over expression of endogenous $H_2O_2$ in living mice with high contrast. This is the first in-vivo imaging afforded by a chemiluminescent small molecular probe that emits NIR light by a direct emission mechanism.

What is claimed is:

1. A compound of the formula Ia or Ib:

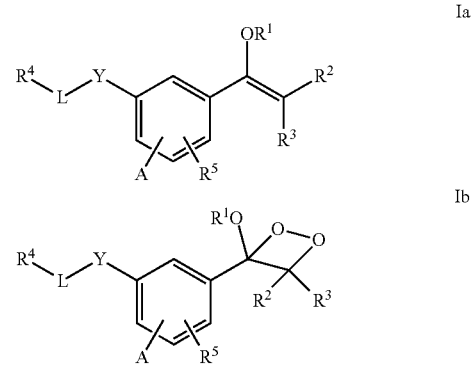

wherein $R^1$ is selected from the group consisting of a linear or branched ($C_1$-$C_{18}$)alkyl, and ($C_3$-$C_7$)cycloalkyl;

$R^2$ and $R^3$ each independently is selected from the group consisting of a branched ($C_3$-$C_{18}$)alkyl and ($C_3$-$C_7$)cycloalkyl, or $R^2$ and $R^3$ together with the carbon atom to which they are attached form a fused, spiro or bridged cyclic or polycyclic ring, $R^4$ is H, or a caging group;

L is absent or is a linker of the formula L1, L2 or L3, optionally substituted at the aromatic ring with one or more substituents each independently selected from the group consisting of ($C_1$-$C_{18}$)alkyl and ($C_3$-$C_7$)cycloalkyl, wherein M is absent or is —O— or —NH—, and the asterisk represents the point of attachment to the group Y, provided that M is —O— or —NH— unless $R^4$ is 4,4,5,5-tetramethyl-1,3,2-dioxaborolanyl or —B(OH)$_2$, and when $R^4$ is H, L is absent;

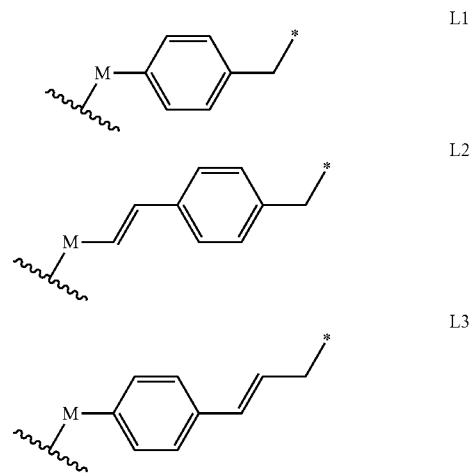

Y is absent or is —O—, provided that Y is —O— unless $R^4$ is 4,4,5,5-tetramethyl-1,3,2-dioxaborolanyl or —B(OH)$_2$, and L is absent;

$R^5$ is H, or represents at least one electron acceptor group such as halogen, —NO$_2$, —CN, —COOR$^6$, —C(=O)

$R^6$ and —$SO_2R^6$, each independently attached either ortho or para to the —Y-L-$R^4$ group;

$R^6$ each independently is H or —($C_1$-$C_{18}$)alkyl; and

A represents one or two π* acceptor groups, each independently attached either ortho or para to the —Y-L-$R^4$ group and selected from the group consisting of —CN and —CH═CH-E, wherein E is (a) —CN, —COOH, or —COO($C_1$-$C_{18}$)alkyl optionally interrupted in the alkylene chain with one or more —O— groups; (b) 4-pyridinyl, methylpyridinium-4-yl, 3,3-dimethyl-3H-indolyl, or 1,3,3-trimethyl-3H-indol-1-ium-2-yl, optionally substituted at one or more of the carbon atoms of the aromatic or heteroaromatic ring with a substituent each independently selected from the group consisting of halogen, —CN, —COOH, —COOR, and —C(O)R, wherein R is —($C_1$-$C_{18}$)alkyl; (c) 4-(dicyanomethylene)-4H-chromen-2-yl, 4H-chromen-2-yl-4-one, 9-(dicyanomethylene)-9H-xanthen-3-yl, 9H-xanthen-3-yl-9-one, 2-dicyanomethylenemethyl-thieno[3,2-b]thiophene-5-yl, 3-methylbenzo[d]thiazol-2-yl-3-ium, tetrathiafulvalenyl, 1,2,3,5,6,7-hexahydropyrido[3,2,1-ij]quinolin-9-yl, benzo[d]oxazol-2-yl, benzo[d]thiazol-2-yl, 1H-benzo[d]imidazol-2-yl, 2,6-di-tert-butylpyrylium-4-yl, 1-methylquinolin-1-ium-4-yl, or 4-dicyanomethylene-2-methyl-4H-pyran-6-yl, optionally substituted at one or more of the carbon atoms of the aromatic or heteroaromatic ring with a substituent each independently selected from the group consisting of halogen, —CN, —COOH, —COOR, and —C(O)R, wherein R is —($C_1$-$C_{18}$)alkyl; or (d) 5,5-dimethyl-3-cyano-2-dicyanomethylene-2,5-dihydrofuran-4-yl, or 5,5-dimethyl-3-cyano-2-oxo-2,5-dihydrofuran-4-yl, provided that at least one of said π* acceptor groups is —CH═CH-E, wherein E is selected from groups (c) and (d).

2. The compound of claim 1, wherein:

(i) $R^1$ is a linear or branched ($C_1$-$C_8$)alkyl; or (ii) $R^2$ and $R^3$ together with the carbon atom to which they are attached form a fused, spiro or bridged polycyclic ring; or (iii) said caging group is selected from the group consisting of:

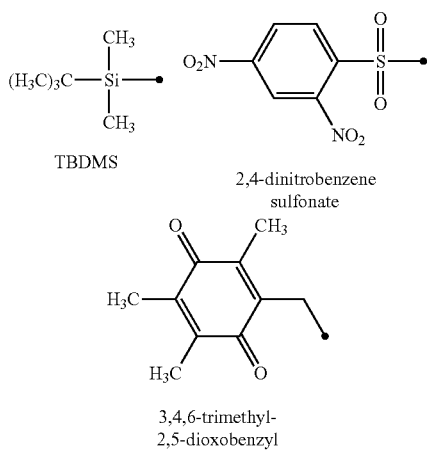

TBDMS 2,4-dinitrobenzene sulfonate 3,4,6-trimethyl-2,5-dioxobenzyl

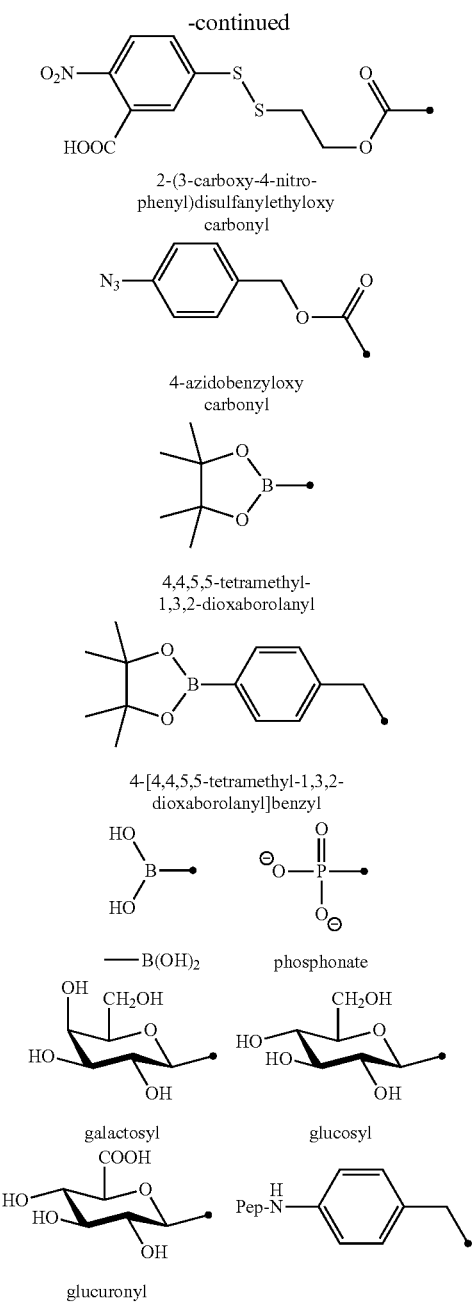

2-(3-carboxy-4-nitrophenyl)disulfanylethyloxy carbonyl 4-azidobenzyloxy carbonyl 4,4,5,5-tetramethyl-1,3,2-dioxaborolanyl 4-[4,4,5,5-tetramethyl-1,3,2-dioxaborolanyl]benzyl B(OH)₂      phosphonate galactosyl      glucosyl glucuronyl wherein Pep is a group comprising a peptide moiety consisting of at least two amino acid residues and linked to the aniline group via a carboxylic group of said peptide moiety; or (iv) $R^5$ is H, or an electron acceptor group selected from the group consisting of halogen and —CN, attached either ortho or para to the —Y-L-$R^4$ group.

3. The compound of claim 2, wherein $R^2$ and $R^3$ together with the carbon atom to which they are attached form adamantyl.

4. The compound of claim 2, wherein $R^5$ is halogen or —CN, attached ortho to the —Y-L-$R^4$ group.

5. The compound of claim 1, wherein A represents one or two π* acceptor groups, wherein:

(i) one of said π* acceptor groups is of the formula —CH═CH-E, wherein E is (a) 4-(dicyanomethylene)-

4H-chromen-2-yl, 4H-chromen-2-yl-4-one, 9-(dicyanomethylene)-9H-xanthen-3-yl, 9H-xanthen-3-yl-9-one, 2-dicyanomethylenemethyl-thieno[3,2-b]thiophene-5-yl, 3-methylbenzo[d]thiazol-2-yl-3-ium, tetrathiafulvalenyl, 1,2,3,5,6,7-hexahydropyrido[3,2,1-ij]quinolin-9-yl, benzo[d]oxazol-2-yl, benzo[d]thiazol-2-yl, 1H-benzo[d]imidazol-2-yl, 2,6-di-tert-butylpyrylium-4-yl, 1-methylquinolin-1-ium-4-yl, or 4-dicyanomethylene-2-methyl-4H-pyran-6-yl, optionally substituted at one or more of the carbon atoms of the aromatic or heteroaromatic ring; or (b) 5,5-dimethyl-3-cyano-2-dicyanomethylene-2,5-dihydrofuran-4-yl, or 5,5-dimethyl-3-cyano-2-oxo-2,5-dihydrofuran-4-yl; and (ii) the other one of said π* acceptor groups, when present, is of the formula —CH=CH-E, wherein E is —CN, —COOH, or —COO($C_1$-$C_{18}$)alkyl optionally interrupted in the alkylene chain with one or more —O— groups.

6. The compound of claim 5, wherein:
(i) one of said π* acceptor groups is of the formula —CH=CH-E, wherein E is 4-(dicyanomethylene)-4H-chromen-2-yl optionally substituted at one or more of the carbon atoms of the aromatic or heteroaromatic ring, or 5,5-dimethyl-3-cyano-2-dicyanomethylene-2,5-dihydrofuran-4-yl; and
(ii) the other one of said π* acceptor groups, when present, is of the formula —CH=CH-E, wherein E is —CN, —COOH, or —COO($C_1$-$C_{18}$)alkyl optionally interrupted in the alkylene chain with one or more —O— groups.

7. The compound of claim 1, wherein:
$R^1$ is a linear or branched ($C_1$-$C_8$)alkyl;
$R^2$ and $R^3$ together with the carbon atom to which they are attached form a fused, spiro or bridged polycyclic ring;
$R^5$ is H, or an electron acceptor group selected from the group consisting of halogen and —CN, attached either ortho or para to the —Y-L-$R^4$ group; and
A represents one or two π* acceptor groups, wherein
(i) one of said π* acceptor groups is of the formula —CH=CH-E, wherein E is (a) 4-(dicyanomethylene)-4H-chromen-2-yl, 4H-chromen-2-yl-4-one, 9-(dicyanomethylene)-9H-xanthen-3-yl, 9H-xanthen-3-yl-9-one, 2-dicyanomethylenemethyl-thieno[3,2-b]thiophene-5-yl, 3-methylbenzo[d]thiazol-2-yl-3-ium, tetrathiafulvalenyl, 1,2,3,5,6,7-hexahydropyrido[3,2,1-ij]quinolin-9-yl, benzo[d]oxazol-2-yl, benzo[d]thiazol-2-yl, 1H-benzo[d]imidazol-2-yl, 2,6-di-tert-butylpyrylium-4-yl, 1-methylquinolin-1-ium-4-yl, or 4-dicyanomethylene-2-methyl-4H-pyran-6-yl, optionally substituted at one or more of the carbon atoms of the aromatic or heteroaromatic ring; or (b) 5,5-dimethyl-3-cyano-2-dicyanomethylene-2,5-dihydrofuran-4-yl, or 5,5-dimethyl-3-cyano-2-oxo-2,5-dihydrofuran-4-yl; and
(ii) the other one of said π* acceptor groups, when present, is of the formula —CH=CH-E, wherein E is —CN, —COOH, or —COO($C_1$-$C_{18}$)alkyl optionally interrupted in the alkylene chain with one or more —O— groups.

8. The compound of claim 7, wherein:
$R^1$ is methyl, ethyl, or isopropyl;
$R^2$ and $R^3$ together with the carbon atom to which they are attached form adamantyl;
$R^5$ is H, or is an electron acceptor group selected from the group consisting of halogen and —CN, attached ortho to the —Y-L-$R^4$ group; and A represents one or two π* acceptor groups, wherein one of said π* acceptor groups is of the formula —CH=CH-E, wherein E is 4-(dicyanomethylene)-4H-chromen-2-yl, or 5,5-dimethyl-3-cyano-2-dicyanomethylene-2,5-dihydrofuran-4-yl; and the other one of said π* acceptor groups, when present, is of the formula —CH=CH-E, wherein E is —CN, —COOH, —COOCH$_3$, —COOC(CH$_3$)$_3$, or —COO[(CH$_2$)$_2$—O]$_4$—CH$_3$.

9. The compound of claim 1, wherein
(i) Y is —O—; L is absent; and $R^4$ is H;
(ii) Y is —O—; L is absent; and $R^4$ is a caging group such as phosphonate and galactosyl;
(iii) Y is —O—, L is absent or a linker of the formula L1, L2 or L3, wherein M is —O— or —NH—, and $R^4$ is a caging group such as galactosyl; or
(iv) Y is absent, L is absent, and $R^4$ is 4,4,5,5-tetramethyl-1,3,2-dioxaborolanyl or —B(OH)$_2$.

10. The compound of claim 1, wherein Y is —O—; L is absent; and $R^4$ is a caging group of the formula:

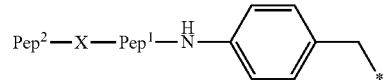

wherein Pep$^1$ is a protease cleavable peptide moiety consisting of at least two amino acid residues and linked via a carboxylic group thereof to the aniline group, wherein said protease cleavable peptide moiety is optionally protected or linked through an amino group thereof to a PEG-containing group; X is absent, or is a linker linked to Pep$^1$ via an amide bond through either a carboxyl or amino group of Pep$^1$; and Pep$^2$ is absent, or a cell-penetrating peptide moiety linked to X either via an amide bond through an amino or carboxyl group thereof, or through a thiol group thereof, provided that X and Pep$^2$ are both either absent or present, and when Pep$^1$ is protected or linked to a PEG-containing group, X and Pep$^2$ are absent.

11. The compound of claim 10, wherein Pep$^1$ is a peptide moiety comprising the amino acid sequence Val-Cit, Phe-Lys, Gly-Phe-Leu-Gly, Gly-Gly-Pro-Nle, Ala-Ala-Asn or His-Ser-Ser-Lys-Leu-Gln, wherein said amino acid sequence is linked via the carboxylic group of the citrulline, lysine, glycine, norleucine, asparagine or glutamine, respectively, to the aniline group; and optionally protected at an amino group thereof, or linked via an amide bond and through said amino group to a PEG-containing group.

12. The compound of claim 11, wherein said PEG-containing group is of the formula

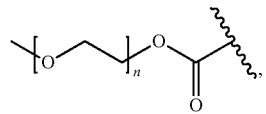

wherein n is an integer of 1 to 227.

13. The compound of claim 11, wherein Pep$^1$ is a peptide moiety of the sequence Val-Cit, Phe-Lys, Gly-Phe-Leu-Gly, Gly-Gly-Pro-Nle, Ala-Ala-Asn or His-Ser-Ser-Lys-Leu-Gln, linked via the carboxylic group of the citrulline, lysine, glycine, norleucine, asparagine or glutamine, respectively, to the aniline group; and either (i) protected at the α-amino group of the valine, phenylalanine, glycine, glycine, alanine or histidine, respectively, with an amino protecting group; or (ii) linked via the α-amino group of the valine, phenylalanine, glycine, glycine, alanine or histidine, respectively, to a PEG-containing group of the formula

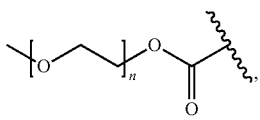

wherein n is an integer of 1 to 227.

14. The compound of claim 10, wherein $Pep^1$ is a peptide moiety comprising the amino acid sequence Val-Cit, Phe-Lys, Gly-Phe-Leu-Gly, Gly-Gly-Pro-Nle, Ala-Ala-Asn or His-Ser-Ser-Lys-Leu-Gln, linked via the carboxylic group of the citrulline, lysine, glycine, norleucine, asparagine or glutamine, respectively, to the aniline group; X is a linker linked to $Pep^1$ via an amide bond through either a carboxyl or amino group of $Pep^1$; and $Pep^2$ is a peptide moiety linked to X through a thiol group thereof.

15. The compound of claim 14, wherein X is a linker of the formula:

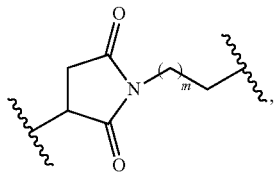

linked to $Pep^1$ via an amide bond through an amino group of $Pep^1$, wherein m is an integer of 1-20, and the alkylene chain of X is optionally interrupted with one or more —O— groups; and $Pep^2$ is a peptide moiety of the sequence Cys-Gly-Lys-Arg-Lys, linked to X through the thiol group of the cysteine residue.

16. The compound of claim 9, wherein $R^1$ is methyl; $R^2$ and $R^3$ together with the carbon atom to which they are attached form adamantyl; and (i) $R^5$ is H; A represents a π* acceptor group of the formula —CH=CH-E attached para to the —Y-L-$R^4$ group, wherein E is 4-(dicyanomethylene)-4H-chromen-2-yl; Y is —O—; L is absent; and $R^4$ is H;

(ii) $R^5$ is Cl attached ortho to the —Y-L-$R^4$ group; A represents a π* acceptor group of the formula —CH=CH-E attached ortho to the —Y-L-$R^4$ group, wherein E is 4-(dicyanomethylene)-4H-chromen-2-yl; Y is —O—; L is absent; and $R^4$ is H;

(iii) $R^5$ is H; A represents two π* acceptor groups, wherein one of said π* acceptor groups is attached para to the —Y-L-$R^4$ group and is of the formula —CH=CH-E, wherein E is 4-(dicyanomethylene)-4H-chromen-2-yl, and the other one of said π* acceptor groups is attached ortho to the —Y-L-$R^4$ group and is of the formula —CH=CH-E, wherein E is —COOH; Y is —O—; L is absent; and $R^4$ is H;

(iv) $R^5$ is H; A represents two π* acceptor groups, wherein one of said π* acceptor groups is attached para to the —Y-L-$R^4$ group and is of the formula —CH=CH-E, wherein E is 5,5-dimethyl-3-cyano-2-dicyanomethyl-ene-2,5-dihydrofuran-4-yl, and the other one of said π* acceptor groups is attached ortho to the —Y-L-$R^4$ group and is of the formula —CH=CH-E, wherein E is —COOH; Y is —O—; L is absent; and $R^4$ is H;

(v) $R^5$ is H; A represents a π* acceptor group of the formula —CH=CH-E attached para to the —Y-L-$R^4$ group, wherein E is 4-(dicyanomethylene)-4H-chromen-2-yl; Y is —O—; L is absent; and $R^4$ is galactosyl;

(vi) $R^5$ is H; A represents two π* acceptor groups, wherein one of said π* acceptor groups is attached para to the —Y-L-$R^4$ group and is of the formula —CH=CH-E, wherein E is 4-(dicyanomethylene)-4H-chromen-2-yl, and the other one of said π* acceptor groups is attached ortho to the —Y-L-$R^4$ group and is of the formula —CH=CH-E, wherein E is —COOH; Y is absent; L is absent; and $R^4$ is 4,4,5,5-tetramethyl-1,3,2-dioxaborolanyl; or (vii) $R^5$ is H; A represents two π* acceptor groups, wherein one of said π* acceptor groups is attached para to the —Y-L-$R^4$ group and is of the formula —CH=CH-E, wherein E is 5,5-dimethyl-3-cyano-2-dicyanomethylene-2,5-dihydrofuran-4-yl, and the other one of said π* acceptor groups is attached ortho to the —Y-L-$R^4$ group and is of the formula —CH=CH-E, wherein E is —COO[$(CH_2)_2$—O]$_4$—$CH_3$; Y is —O—; L is L1 wherein M is —O—; and $R^4$ is galactosyl.

17. The compound of claim 16, selected from the group consisting of Luminophore 1, Luminophore 2, Luminophore 3, Luminophore 4, Probe 1a, Probe 2a, and Probe 3a:

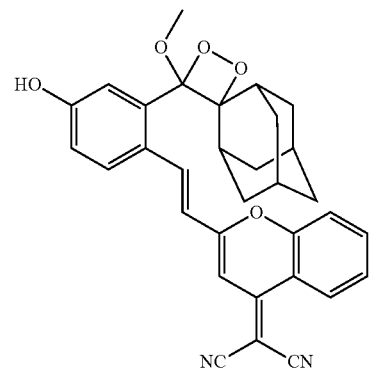

Luminophore 1

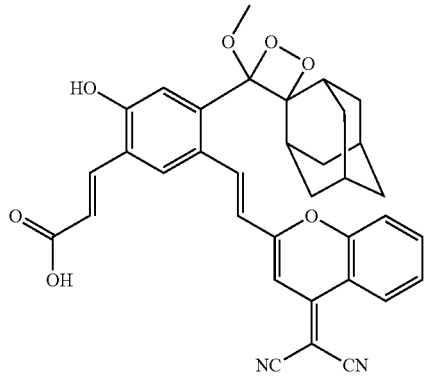

Luminophore 2

Luminophore 3
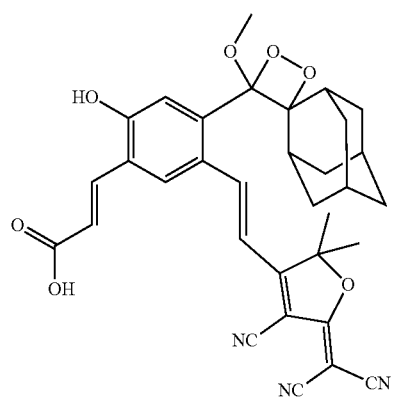
Luminophore 4
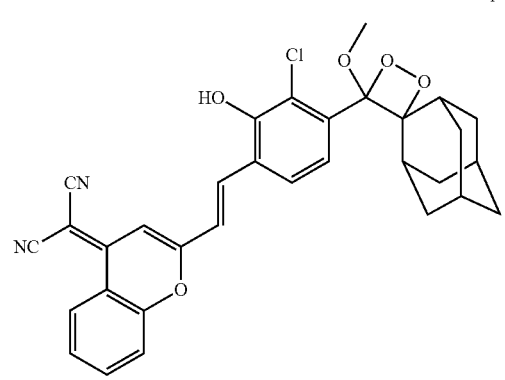
Probe 1a
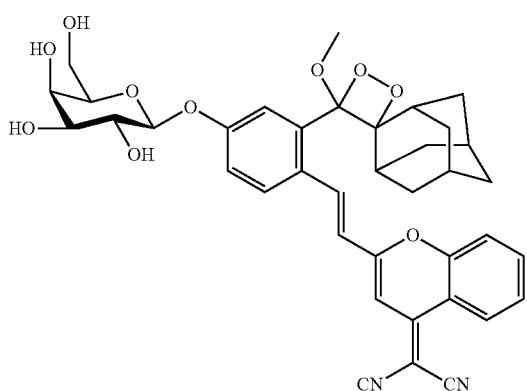
Probe 2a
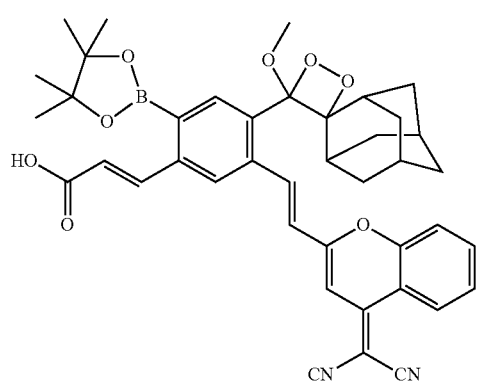
Probe 3a
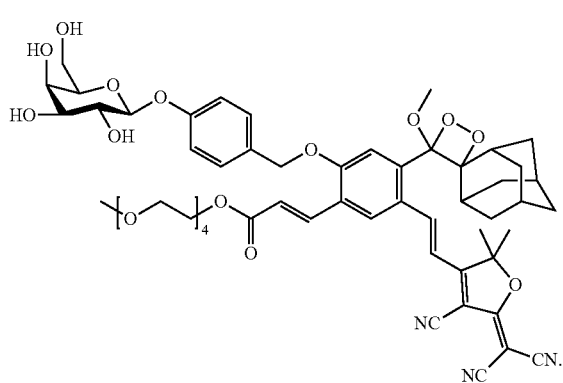
18. A composition comprising a compound according to claim 1, and a carrier.
19. The composition of claim 18, comprising a compound selected from the group consisting of Luminophore 1, Luminophore 2, Luminophore 3, Luminophore 4, Probe 1a, Probe 2a, and Probe 3a:
Luminophore 1
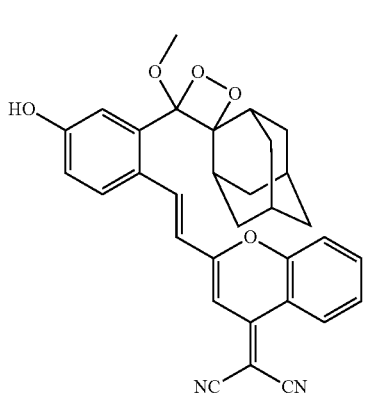
Luminophore 2
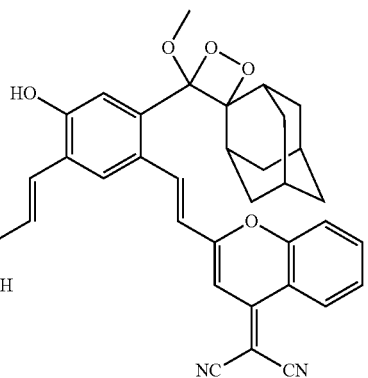

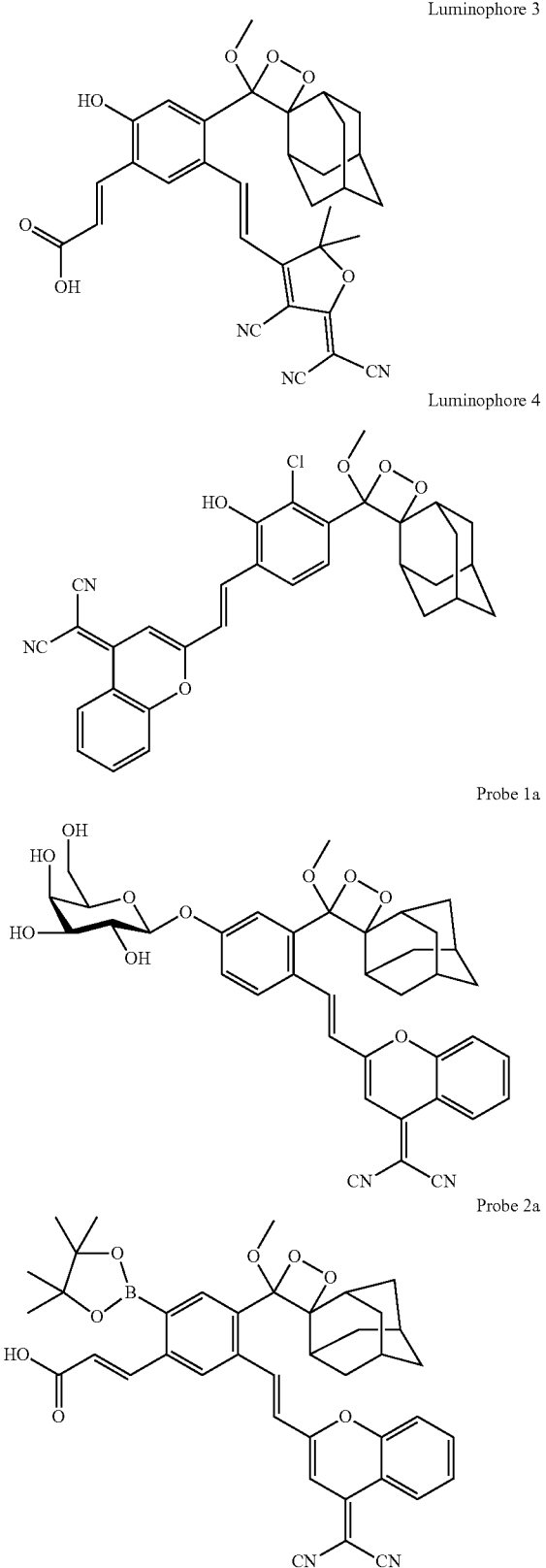
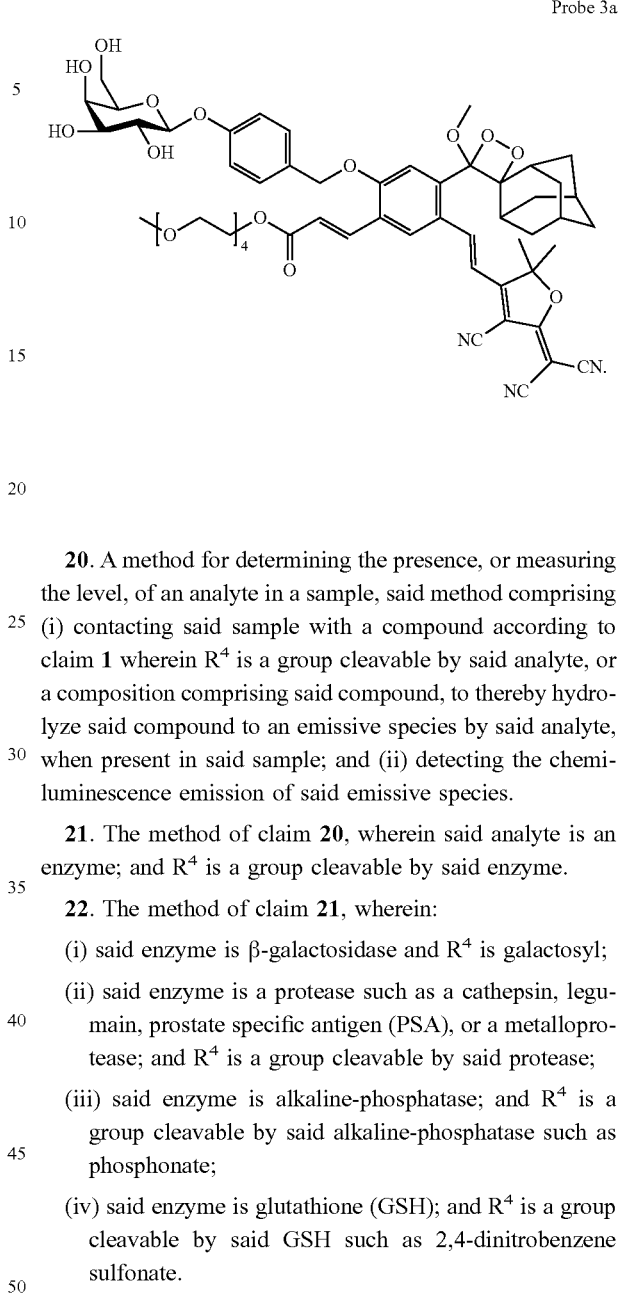

20. A method for determining the presence, or measuring the level, of an analyte in a sample, said method comprising (i) contacting said sample with a compound according to claim 1 wherein $R^4$ is a group cleavable by said analyte, or a composition comprising said compound, to thereby hydrolyze said compound to an emissive species by said analyte, when present in said sample; and (ii) detecting the chemiluminescence emission of said emissive species.

21. The method of claim 20, wherein said analyte is an enzyme; and $R^4$ is a group cleavable by said enzyme.

22. The method of claim 21, wherein:

(i) said enzyme is β-galactosidase and $R^4$ is galactosyl;

(ii) said enzyme is a protease such as a cathepsin, legumain, prostate specific antigen (PSA), or a metalloprotease; and $R^4$ is a group cleavable by said protease;

(iii) said enzyme is alkaline-phosphatase; and $R^4$ is a group cleavable by said alkaline-phosphatase such as phosphonate;

(iv) said enzyme is glutathione (GSH); and $R^4$ is a group cleavable by said GSH such as 2,4-dinitrobenzene sulfonate.

23. The method of claim 20, wherein said analyte is hydrogen peroxide; and $R^4$ is 4,4,5,5-tetramethyl-1,3,2-dioxaborolanyl, or 4-[4,4,5,5-tetramethyl-1,3,2-dioxaborolanyl]benzyl.

24. The method of claim 20, wherein said sample is a biological sample.

25. The method of claim 24, wherein said biological sample is a bodily fluid, a bodily fluid-based solution, or a tissue biopsy sample.

* * * * *

UNITED STATES PATENT AND TRADEMARK OFFICE
CERTIFICATE OF CORRECTION

PATENT NO. : 11,241,507 B2
APPLICATION NO. : 16/616336
DATED : February 8, 2022
INVENTOR(S) : Doron Shabat It is certified that error appears in the above-identified patent and that said Letters Patent is hereby corrected as shown below:

On the Title Page

Column 2 (Item (57) Abstract), Line 2, delete "Schapp's" and insert --Schaap's--.

In the Specification

Column 2, Line 4, delete "adamatylidene" and insert --adamantylidene--.

Column 2, Line 56-67 (approx.), delete " 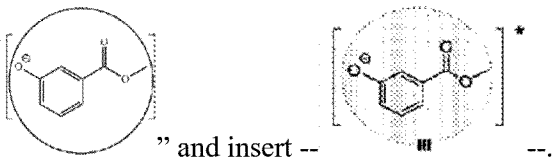 " and insert --   --.

Column 3, Line 12 (approx.), delete "Schapp's" and insert --Schaap's--.

Column 3, Line 15 (approx.), delete "Schapp's" and insert --Schaap's--.

Column 3, Line 32 (approx.), delete "Schapp's" and insert --Schaap's--.

Column 7, Line 10, delete "Heck293" and insert --HEK293--.

Column 8, Line 24-25, delete "γ-aminobutiric" and insert --γ-aminobutyric--.

Column 16, Line 53, delete "G H," and insert --G, H,--.

Column 18, Line 46, delete "7∏*" and insert --∏*--.

Column 27, Line 38, delete "(072" and insert --0.72--.

Signed and Sealed this
Second Day of August, 2022

Katherine Kelly Vidal
*Director of the United States Patent and Trademark Office*

CERTIFICATE OF CORRECTION (continued)
U.S. Pat. No. 11,241,507 B2

Column 30, Line 58-65 (approx.), delete " 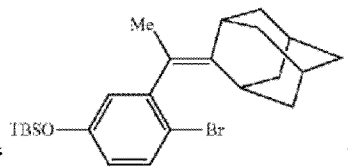 " and insert
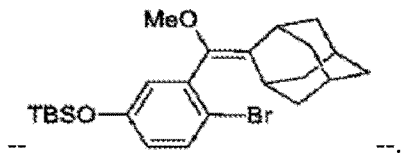 --.

Column 31, Line 1-9 (approx.), delete " 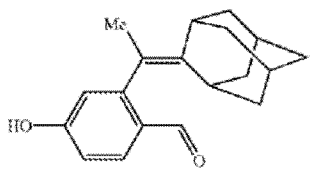 " and insert
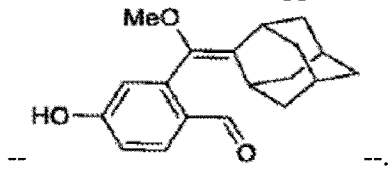 --.

Column 34, Line 55, delete "the" and insert --The--.

Column 38, Line 38 (approx.), delete "δ10.11" and insert --δ 10.11--.

Column 38, Line 41 (approx.), delete "δ191.39," and insert --δ 191.39,--.

Column 38, Line 53 (approx.), delete "Iodomehtane," and insert --Iodomethane,--.

Column 42, Line 48 (approx.), delete "liminophore's" and insert --luminophore's--.